US009554755B2

(12) United States Patent
Mwanza et al.

(10) Patent No.: US 9,554,755 B2
(45) Date of Patent: Jan. 31, 2017

(54) METHODS, SYSTEMS, AND COMPUTER READABLE MEDIA FOR PREDICTING EARLY ONSET GLAUCOMA

(71) Applicant: The University of North Carolina at Chapel Hill, Chapel Hill, NC (US)

(72) Inventors: Jean-Claude Kasongo Mwanza, Chapel Hill, NC (US); Donald Lyle Budenz, Chapel Hill, NC (US); Joshua Lindsey Warren, New Haven, CT (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 14/881,972

(22) Filed: Oct. 13, 2015

(65) Prior Publication Data

US 2016/0100806 A1    Apr. 14, 2016

Related U.S. Application Data

(60) Provisional application No. 62/063,335, filed on Oct. 13, 2014.

(51) Int. Cl.
*A61B 3/10* (2006.01)
*A61B 3/00* (2006.01)
*A61B 5/00* (2006.01)

(52) U.S. Cl.
CPC .......... *A61B 5/7275* (2013.01); *A61B 3/0025* (2013.01); *A61B 3/102* (2013.01)

(58) Field of Classification Search
USPC ................................................ 351/205, 246
See application file for complete search history.

(56) References Cited

U.S. PATENT DOCUMENTS 8,721,077 B2 *  5/2014  Vermeer ................ A61B 3/102
                                                         351/205

OTHER PUBLICATIONS

Mwanza et al., "Combining Spectral Domain Optical Coherence Tomography Structural Parameters for the Diagnosis of Glaucoma With Early Visual Field Loss," Invest Ophthalmol Vis Sci., vol. 54, pp. 8393-8400 (2013).
Mwanza et al., "Glaucoma Diagnostic Accuracy of Ganglion Cell-Inner Plexiform Layer Thickness: Comparison with Nerve Fiber Layer and Optic Nerve Head," American Academy of Ophthalmology, vol. 119, pp. 1151-1158 (2012).

(Continued)

*Primary Examiner* — Jack Dinh
(74) *Attorney, Agent, or Firm* — Jenkins, Wilson, Taylor & Hunt, P.A.

(57) ABSTRACT

Methods, systems, and computer readable media for predicting early onset glaucoma via structural parameters obtained via time and spectral-domain optical coherence tomography (SD-OCT) are disclosed. SD-OCT technology measures the thicknesses of the layers of the retina that contain the cells that die in glaucoma before there is any functional loss. A multivariable predictive model may be used for the diagnosis of early glaucoma using a combination of optic nerve head (ONH), peripapillary retinal nerve fiber layer (RNFL), and macular ganglion cell-inner plexiform layer (GCIPL) parameters measured via SD-OCT. The model generates a glaucoma probability score for individual patient, which is valuable information in assisting clinicians in glaucoma diagnosis and treatment.

19 Claims, 6 Drawing Sheets

(56) References Cited

OTHER PUBLICATIONS

Fang et al., "Diagnostic capability of Fourier-Domain optical coherence tomography in early primary open angle glaucoma," Chinese Medical Journal, vol. 123, No. 15, pp. 2045-2050 (2010).
Hair Jr. et al., "Multivariate Data Analysis," Seventh Edition, Upper Saddle River, NJ, Pearson Prentice Hall (2010).
Ferreras et al., "Discriminating between Normal and Glaucoma-Damaged Eyes with the Heidelberg Retina Tomograph 3," American Academy of Ophthalmology, vol. 115, pp. 775-781 (2008).
Budenz et al., "Sensitivity and Specificity of the StratusOCT for Perimetric Glaucoma," American Academy of Ophthalmology, vol. 112, pp. 3-9 (2005).
Magacho et al., "Discrimination between normal and glaucomatous eyes with scanning laser polarimetry and optic disc topography: A preliminary report," European Journal of Ophthalmology, vol. 15, No. 3, pp. 353-359 (2005).
Friedman et al., "Prevalence of Open-Angle Glaucoma Among Adults in the United States," American Medical Association, vol. 122, No. 4, pp. 532-538 (Apr. 2004).
Azuara-Blanco et al., "Clinical Agreement Among Glaucoma Experts in the Detection of Glaucomatous Changes of the Optic Disk Using Simultaneous Stereoscopic Photographs," Am J Ophthalmol, vol. 136, pp. 949-950 (2003).
Ford et al., "Comparison of Data Analysis Tools for Detection of Glaucoma with the Heidelberg Retina Tomograph," American Academy of Ophthalmology, vol. 110, pp. 1145-1150 (2003).
Gorsuch, "Exploratory Factor Analysis: Its Role in Item Analysis," Journal of Personality Assessment, vol. 68, No. 3, pp. 532-560 (1997).
Mikelberg et al., "Optic Nerve Axon Count and Axon Diameter in Patients with Ocular Hypertension and Normal Visual Fields," Ophthalmology vol. 102, pp. 342-348 (1995).
Gorsuch, "Common Factor Analysis versus Component Analysis: Some Well and Little Known Facts," Multivariate Behavioral Research, vol. 25, No. 1, pp. 33-39 (1990).
McArdle, "Principles versus Principals of Structural Factor Analyses," Multivariate Behavioral Research, vol. 25, No. 1, pp. 81-87 (1990).
Quigley et al., "Optic Nerve Damage in Human Glaucoma," Arch. Ophthalmology, vol. 100, pp. 135-146 (Jan. 1982).
Wang et al., "Combining Information from Three Anatomic Regions in the Diagnosis of Glaucoma with Time-Domain Optical Coherence Tomography," J Glaucoma, pp. 1-15 (Mar. 2014).
Tielsch et al., "Intraobserver and interobserver agreement in measurement of optic disc characteristics," Ophthalmology, vol. 95, pp. 350-356 (1988).
Baskaran et al., "Classification Algorithms Enhance the Discrimination of Glaucoma from Normal Eyes Using High-Definition Optical Coherence Tomography," Investigative Ophthalmology & Visual Science, vol. 53, No. 4, pp. 2314-2320 (Apr. 2012).
Mwanza et al., "Macular Ganglion Cell-Inner Plexiform Layer: Automated Detection and Thickness Reproducibility with Spectral Domain-Optical Coherence Tomography in Glaucoma," Investigative Ophthalmology & Visual Science, vol. 52, No. 11, pp. 8323-8329 (Oct. 2011).
Mwanza et al., "Ability of Cirrus™ HD-OCT Optic Nerve Head Parameters to Discriminate Normal from Glaucomatous Eyes," Ophthalmology, vol. 118, No. 2, pp. 241-248 (Feb. 2011).
Huang et al., "Diagnostic Power of Optic Disc Morphology, Peripapillary Retinal Nerve Fiber Layer Thickness, and Macular Inner Retinal Layer Thickness in Glaucoma Diagnosis With Fourier-domain Optical Coherence Tomography," Journal of Glaucoma, vol. 20, No. 2, pp. 87-94 (Feb. 2011).
Tóth et al., "Accuracy of Scanning Laser Polarimetry, Scanning Laser Tomography, and Their Combination in a Glaucoma Screening Trial," Journal of Glaucoma, vol. 17, No. 8, pp. 639-646 (Dec. 2008).
Lu et al., "Combining Nerve Fiber Layer to Optimize Glaucoma Diagnosis with Optical Coherence Tomography," Ophthalmology, vol. 115, No. 8, pp. 1352-1357 (Aug. 2008).
Badalà et al., "Optic Disc and Nerve Fiber Layer Imaging to Detect Glaucoma," Am J Ophthalmol., vol. 144, No. 5, pp. 724-732 (Nov. 2007).
Quigley et al., "The number of people with glaucoma worldwide in 2010 and 2020," Br J Ophthalmol, vol. 90, pp. 262-267 (2006).
Huang et al., "Development and Comparison of Automated Classifiers for Glaucoma Diagnosis Using Stratus Optical Coherence Tomography," Investigative Ophthalmology & Visual Science, vol. 46, No. 11, pp. 4121-4129 (Nov. 2005).
Medeiros et al., "Evaluation of Retinal Nerve Fiber Layer, Optic Nerve Head, and Macular Thickness Measurements for Glaucoma Detection Using Optical Coherence Tomography," Am J Ophthalmol, vol. 139, No. 1, pp. 44-55 (2005).
Kingman, "Glaucoma is second leading cause of blindness globally," Bulletin of the World Health Organization, vol. 82, No. 11, pp. 887-888 (Nov. 2004).
Burnham et al.. "Multimodel Inference: Understanding AIC and BIC in Model Selection," Sociological Methods & Research, vol. 33, No. 2, pp. 261-304 (Nov. 2004).
Iester et al., "Discriminant Analysis Formulas of Optic Nerve Head Parameters Measured by Confocal Scanning Laser Tomography," Journal of Glaucoma, vol. 11, No. 2, pp. 97-104 (2002).
Iester et al., "Discriminant Analysis Models for Early Glaucoma Detection of Glaucomatous Optic Disc Changes," Br J Ophthalmol, vol. 84, pp. 464-468 (2000).
Jöreskog, "How Large Can a Standardized Coefficient be?," http://www.ssicentral.com/lisrel/techdocs/HowLargeCanaStandardizedCoefficientbe.pdf., pp. 1-3 (Jun. 22, 1999).
Mardin et al., "Preperimetric Glaucoma Diagnosis by Confocal Scanning Laser Tomography of the Optic Disc," Br J Ophthalmol, vol. 83, pp. 299-304 (1999).
Fabrigar et al., "Evaluating the Use of Explanatory Factor Analysis in Psychological Research," Psychological Methods, vol. 4, No. 3, pp. 272-299 (1999).
Burk et al., "Prediction of Glaucomatous Visual Field Defects by Reference Plane Independent Three-Dimensional Optic Nerve Head Parameters," Proceedings of the XIIIth International Perimetric Society Meeting, pp. 463-474 (Sep. 6-9, 1998).
Bathija et al., "Detection of Early Glaucomatous Structural Damage with Confocal Scanning Laser Tomography," Journal of Glaucoma, vol. 7, No. 2, pp. 121-127 (1998).
Iester et al., "Sector-Based Analysis of Optic Nerve Head Shape Parameters and Visual Field Indices in Healthy and Glaucomatous Eyes," Journal of Glaucoma, vol. 6, No. 6, pp. 371-376 (1997).
Mikelberg et al., "Ability of the Heidelberg Retina Tomograph to Detect Early Glaucomatous Visual Field Loss," Journal of Glaucoma, vol. 4, No. 4, pp. 242-247 (1995).
DeLong et al., "Comparing the Areas Under Two or More Correlated Receiver Operating Characteristic Curves: A Nonparametric Approach," Biometrics, vol. 44, pp. 837-845 (Sep. 1988).

* cited by examiner

TABLE 1. Sample Correlation Matrix for All 16 Variables Included in the Analysis (Modeling Set)

| | Average GCIPL | Minimum GCIPL | Superotemporal GCIPL | Superior GCIPL | Superonasal GCIPL | Inferonasal GCIPL | Inferior GCIPL | Inferotemporal GCIPL | Average RNFL | Temporal RNFL | Superior RNFL | Nasal RNFL | Inferonasal RNFL | Rim Area | CDR | VCDR |
|---|---|---|---|---|---|---|---|---|---|---|---|---|---|---|---|---|
| Average GCIPL | 1.000 | 0.936 | 0.918 | 0.913 | 0.913 | 0.931 | 0.923 | 0.886 | 0.781 | 0.604 | 0.710 | 0.361 | 0.696 | 0.660 | -0.496 | -0.522 |
| Minimum GCIPL | | 1.000 | 0.861 | 0.827 | 0.805 | 0.843 | 0.903 | 0.900 | 0.705 | 0.533 | 0.623 | 0.289 | 0.668 | 0.640 | -0.531 | -0.575 |
| Superotemporal GCIPL | | | 1.000 | 0.913 | 0.853 | 0.758 | 0.749 | 0.772 | 0.727 | 0.595 | 0.700 | 0.338 | 0.593 | 0.607 | -0.464 | -0.491 |
| Superior GCIPL | | | | 1.000 | 0.894 | 0.779 | 0.739 | 0.679 | 0.710 | 0.565 | 0.678 | 0.342 | 0.589 | 0.582 | -0.409 | -0.426 |
| Superonasal GCIPL | | | | | 1.000 | 0.865 | 0.740 | 0.669 | 0.671 | 0.571 | 0.614 | 0.368 | 0.539 | 0.502 | -0.355 | -0.365 |
| Inferonasal GCIPL | | | | | | 1.000 | 0.906 | 0.804 | 0.698 | 0.560 | 0.610 | 0.321 | 0.634 | 0.589 | -0.440 | -0.453 |
| Inferior GCIPL | | | | | | | 1.000 | 0.931 | 0.723 | 0.526 | 0.629 | 0.294 | 0.708 | 0.646 | -0.507 | -0.540 |
| Inferotemporal GCIPL | | | | | | | | 1.000 | 0.748 | 0.510 | 0.654 | 0.321 | 0.741 | 0.685 | -0.546 | -0.588 |
| Average RNFL | | | | | | | | | 1.000 | 0.654 | 0.907 | 0.561 | 0.909 | 0.770 | -0.583 | -0.624 |
| Temporal RNFL | | | | | | | | | | 1.000 | 0.517 | 0.059 | 0.493 | 0.483 | -0.474 | -0.486 |
| Superior RNFL | | | | | | | | | | | 1.000 | 0.449 | 0.739 | 0.702 | -0.482 | -0.524 |
| Nasal RNFL | | | | | | | | | | | | 1.000 | 0.420 | 0.369 | -0.232 | -0.228 |
| Inferior RNFL | | | | | | | | | | | | | 1.000 | 0.738 | -0.562 | -0.615 |
| Rim area | | | | | | | | | | | | | | 1.000 | -0.741 | -0.731 |
| CDR | | | | | | | | | | | | | | | 1.000 | 0.978 |
| VCDR | | | | | | | | | | | | | | | | 1.000 |

FIG. 1

TABLE 5. Discriminating Ability of the Multivariable and Single Variable Analyses in Modeling Set and Proportion of Subjects Correctly Classified (%CC) and Median Length of Prediction Intervals (MPLI) in the Validation Set (Controlling for Age of the Subjects)

| Variables | AUC (95% CI) | Sensitivity (90% Spec) | Sensitivity (95% Spec) | AIC | %CC | MLPI |
|---|---|---|---|---|---|---|
| Modeling set | | | | | | |
| EFA GLM | 0.995 (0.989, 1.000) | 100.0 | 98.6 (87.8, 99.8) | 43.29 | - | - |
| VCDR | 0.987 (0.976, 0.998)* | 97.1 (87.0, 99.4) | 89.9 (74.2, 96.5) | 59.64 | - | - |
| Inferior RNFL | 0.943 (0.908, 0.979)† | 82.6 (66.7, 91.8) | 79.7 (60.8, 90.9) | 108.37 | - | - |
| Minimum GCIPL | 0.958 (0.930, 0.987)† | 85.5 (70.4, 93.6) | 78.3 (59.0, 90.0) | 113.16 | - | - |
| Validation set | | | | | | |
| EFA GLM | 0.974 (0.948, 1.000) | 91.4 (70.0, 98.0) | 88.6 (62.5, 97.3) | 43.43 | 91.67 | 0.050 |
| VCDR | 0.969 (0.938, 1.000) | 91.4 (70.0, 98.0) | 88.6 (62.5, 97.3) | 41.90 | 90.48 | 0.095 |
| Inferior RNFL | 0.929 (0.877, 0.981)* | 74.3 (48.8, 89.7) | 65.7 (36.8, 86.3) | 60.32 | 85.71 | 0.130 |
| Minimum GCIPL | 0.862 (0.780, 0.945)† | 60.0 (35.0, 80.7) | 51.4 (25.0, 77.0) | 86.02 | 80.95 | 0.152 |

* Indicates that the AUC is significantly different from the EFA GLM AUC at the 0.1 level of significance.
† Indicates that the AUC is significantly different from the EFA GLM AUC at the 0.05 level of significance.

FIG. 4

METHODS, SYSTEMS, AND COMPUTER READABLE MEDIA FOR PREDICTING EARLY ONSET GLAUCOMA

PRIORITY CLAIM

This application claims the benefit of U.S. Provisional Patent Application Ser. No. 62/063,335, filed Oct. 13, 2014; the disclosure of which is incorporated herein by reference in its entirety.

TECHNICAL FIELD

The subject matter herein generally relates to spectral domain optical coherence tomography (SD-OCT), and more particularly, to methods, systems, and computer readable media for predicting early onset glaucoma via structural parameters obtained via SD-OCT.

BACKGROUND

Glaucoma is the second leading cause of blindness in the world. [1] The loss in vision is irreversible, and recent estimates based on meta-analysis of population-based studies indicate that in 2010 there were 44.7 million people with open-angle glaucoma (OAG) worldwide, and 2.8 million people in the United States. [2] These numbers are projected to reach 58.6 million worldwide [2] and 3.4 million in the United States by 2020. [3]

The current standard for the diagnosis of glaucoma is based on the presence of typical structural changes with corresponding functional deficits. However, studies on early changes in glaucoma have shown that structural changes indicated by significant loss of retinal ganglion cells and their axons may precede detection of functional deficit by currently available standard automated perimetry (SAP) methods. [4, 5] In addition, SAP is subject to fluctuation even in clinically stable glaucoma.

Ophthalmoscopy and optic disc photography traditionally have been used as primary methods for structural assessment in glaucoma. However, substantial interobserver variability and low to medium interobserver agreement in detecting subtle changes makes ophthalmoscopy or fundus photography alone poor methods for detecting changes indicative of early glaucoma or glaucomatous progression. [6, 7]

In recent years, and with the advent and continuous improvement of imaging devices such as scanning laser ophthalmoscopy (SLO), scanning laser polarimetry (SLP), and time and spectral-domain optical coherence tomography (SD-OCT), a great deal of effort has been invested in identifying quantifiable parameters for objective assessment of structural glaucomatous damage. Of these devices, SD-OCT has rapidly become one of the most widely used technologies in daily clinic due to its high image resolution and measurement precision. The caveat, however, is that the clinician is presented with an array of quantitative information to mentally process as part of the diagnosis process. The multitude of parameters—most of which are highly correlated and are redundant to some extent—oftentimes renders the interpretation process difficult, particularly when structural changes conflict in their results.

For example, optic nerve head (ONH) parameters may appear normal but retinal nerve fiber layer (RNFL) measurements may appear abnormal. One way of circumventing this issue would be to use a multivariable model that reduces the number of structural parameters provided by the OCT output into a set of fewer parameters containing the most useful and relevant information from the original set while also explaining a majority of variability in the original dataset. Earlier studies have combined structural parameters measured by one or several of the devices listed above to assess the glaucoma diagnostic ability using various methods such as machine learning classifiers, linear discriminant functions (LDF), and principal component analysis (PCA). [8-12] In addition, three recent studies used linear discriminant analysis to assess diagnostic ability of combined structural parameters measured SD-OCT. One of these studies combined ONH and peripapillary RNFL parameters, [13] whereas the two others used a combination of ONH, peripapillary RNFL, and ganglion cell of complex (GCC) parameters, [14, 15] which is anatomically different from ganglion cell inner-plexiform layer (GCIPL). [16] In view of these studies however, a need still exists for predicting early onset glaucoma in patients.

In view of the existing glaucoma diagnosis methods and studies described above, it can be appreciated that the diagnosis of glaucoma in the early stages is challenging. One of the major obstacles in preventing glaucoma blindness is the failure to identify individuals with the condition in the early stages, when changes are not distinct. Waiting until significant visual function loss has occurred means that 30-50% of the cells have died and cannot be regenerated.

In view of the shortcomings of the existing glaucoma diagnosis methods and studies described above, and further in view of the high number of people affected by glaucoma, a need exists for methods, systems, and computer readable media for predicting early onset glaucoma using a combination of structural parameters measured via SD-OCT.

SUMMARY

Methods, systems, and computer readable media for predicting early onset glaucoma are provided. In one embodiment, a method of predicting early onset glaucoma is provided. The method includes obtaining a set of patient-specific structural parameters via Spectral Domain Optical Coherence Tomography (SD-OCT). The set of patient-specific structural parameters includes Optic Nerve Head (ONH) parameters, peripapillary Retinal Nerve Fiber Layer (RNFL) parameters, and Ganglion Cell-Inner Plexiform Layer (GCIPL) parameters. The method further includes generating a glaucoma probability score based upon the set of patient-specific parameters and a model dataset associated with plurality of patients. The glaucoma probability score is a whole number integer between 0 and 1, which predicts the onset of early glaucoma between approximately 0% and 100%. Patients may be treated based upon the results of the glaucoma probability score.

In one embodiment, a system of predicting early onset glaucoma is provided. The system includes a glaucoma predicting module (GPM) residing at a computing platform node. The GPM is configured to obtain a set of patient-specific structural parameters. The set of parameters includes Optic Nerve Head (ONH) parameters, peripapillary Retinal Nerve Fiber Layer (RNFL) parameters, and Ganglion Cell-Inner Plexiform Layer (GCIPL) parameters measured via Spectral Domain Optical Coherence Tomography (SD-OCT). The GPM is further configured to generate a glaucoma probability score using the set of patient-specific parameters and a model dataset stored in a database. In some embodiments, the GPM transforms the patient-specific parameters via application of the model to predict the glaucoma probability score.

The subject matter described herein may be implemented in hardware, software, firmware, or any combination thereof. As such, the terms "function" "node" or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps.

Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

The subject matter described herein will now be explained with reference to the accompanying drawings of which:

FIG. 1 is a table containing a sample correlation matrix produced by an exploratory factor analysis (EFA) method as described herein and includes 16 continuous variables useful for the analysis and predicting early onset glaucoma;

FIG. 4 is a table indicating the discriminating ability of the multivariable and single variable analyses in a modeling set for validating analysis and prediction of early onset glaucoma;

DETAILED DESCRIPTION

Figure 2:
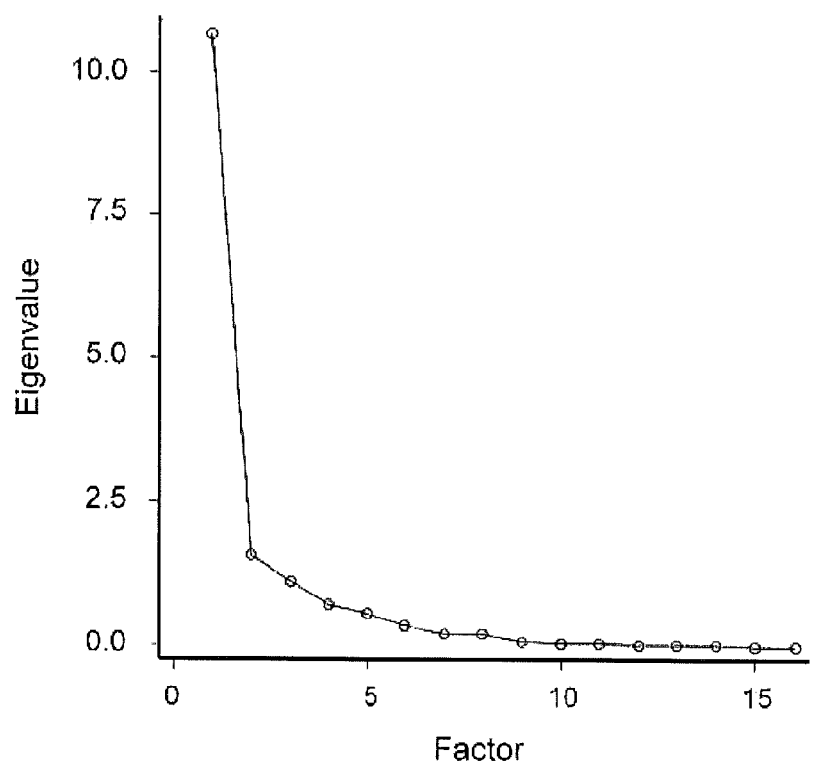
FIG. 2 is a graphical illustration of a scree plot of eigenvalues from the EFA of one or more structural parameters as measured using Spectral Domain Optical Coherence Tomography (SD-OCT)

The subject matter described herein is for methods, systems, and special purpose computers executing computer readable media for predicting early onset glaucoma. Predictions may be made via a multivariable predictive model for glaucoma with early visual field loss using a combination of spectral-domain optical coherence (SD-OCT) parameters.

As described herein, "early" or "early onset" glaucoma indicates the presence of possible ocular structural changes in the absence of perceptible or detectable vision loss and/or functional deficits. That is, detection or prediction of early glaucoma is advantageous, as deficits such as perceptible irreversible vision loss or other perceptible losses in ocular function have not yet occurred and can be preempted.

I. Model Generation

Study Subjects and Database

The data used and/or transformed for generating the model in this study was from subjects who participated in two earlier glaucoma SD-OCT imaging studies [16, 17] and one ongoing study, which obtained institutional review board approval, the procedures of which adhered to the principles of the Declaration of Helsinki for research involving human subjects. Written informed consent was obtained from all participants. Subjects included 104 patients with definitive early glaucoma and 149 normal patients. The dataset was randomly divided into a modeling set (⅔ of the original sample) and a validation set (⅓ of the original sample). A larger sample size for the modeling set was used as the introduced method consists of two stages (factor analysis and multiple logistic regression). The modeling set included 69 early glaucoma patients and 100 normal patients, while the validation set included 35 early-glaucoma patients and 49 normal patients. Both healthy subjects and patients with glaucoma underwent an eligibility complete ophthalmologic examination that included measurement of visual acuity, IOP, and refraction, and biomicroscopy of the anterior segment and dilated fundus examination.

Glaucomatous patients also underwent visual field testing with a Humphrey Visual Field Analyzer (e.g., machine), available for example, from Carl Zeiss Meditec, Inc., of Dublin, Calif., using the Swedish Interactive Thresholding Algorithm standard program. Criteria for the diagnosis of glaucoma were typical glaucomatous optic disc changes with corresponding visual field defects. Optic disc change was indicated by cup-to-disc ratio (CDR) greater than 0.5 in either eye, CDR asymmetry greater than or equal to 0.2, or focal thinning of the rim in either eye.

A glaucomatous visual field defect was defined as glaucoma hemifield test outside normal limits, pattern SD with a P value less than 5%, or a cluster three points or more in the pattern deviation plot in a single hemifield (superior or inferior) with a P value of less than 5%, one of which having a P value of less than 1%. All participants were excluded based on best-corrected visual acuity worse than 20/40 in either eye, refraction error outside the interval −12 to +8 spherical diopters (D) or worse than 3 cylindrical D, active infection of the anterior or posterior segment of either eye, previous or current vitreoretinal diseases or surgery in the study eye, or evidence of diabetic retinopathy or macular edema on dilated ophthalmoscopic examination or retinal photograph evaluation. In addition, glaucoma patients were excluded if the visual field MD was worse than −6 dB. Only one randomly selected eye was tested for the study from each participant.

OCT Imaging

Subjects underwent imaging using an imaging machine, such as a Cirrus HD-OCT, available, for example, from Carl Zeiss Meditec, Inc., macular (Macular Cube 2003200 protocol) and optic disc (Optic Disc Cube 2003200 protocol) scans. All scans were visually reviewed for quality control, and only scans with signal strength greater than or equal to 6, without RNFL misalignment or discontinuity, blinking or involuntary saccade artifacts, and an absence of algorithm segmentation failure on careful visual inspection were retained for analysis. The macular scan was used to measure the thickness of the GCIPL, whereas the optic disc scan served for measuring peripapillary RNFL and optic disc topography. [16, 17] Peripapillary RNFL variables considered for analysis were average and quadrant (superior, nasal, inferior, and temporal) thicknesses. Ganglion cell inner-plexiform layer thickness variables included average, minimum (minimum of the average GCIPL thickness along a given radial spoke in the elliptical annulus), [18] and sectoral (superior, superonasal, inferonasal, inferior, inferotemporal, and superotemporal) thicknesses. Parameters from the ONH analysis included rim area, CDR, and vertical cup-to-disc diameter ratio (VCDR).

Data Management and Statistical Analysis

Statistical analysis was performed to determine which variables (i.e., of 16 total) to use in a glaucoma prediction model. Pearson's correlation coefficient was calculated to explore pairwise linear relationships between the 16 (5 RNFL, 3 ONH, and 8 GCIPL) continuous variables used for analysis in this study, as a preparatory step for factor analysis. Factor analysis was subsequently performed on the data set of 16 variables using the method of exploratory factor analysis (EFA) with a promax rotation to identify latent factors accounting for a large proportion of the variability seen in the original set of variables. Use of the oblique promax rotation resulted in an improved interpretation of latent factors, which are not uniquely identified. It was preferred over other orthogonal rotation methods (varimax, equamax, orthomax, quartimax, and parsimax) in this setting, due to its ability to reduce crossloadings, which lead to improved factor interpretations and its similar performance in the multiple logistic regression models using a varying number of retained factors.

During the EFA, standardized scoring coefficients are estimated for each factor and variable combination. A set of coefficients for a chosen factor serves as a weight for each variable and is multiplied by each person's standardized variable response. These weighted values are then summed to create the estimated factor score for a person. This process is repeated for each factor and each person in order to obtain the complete set of estimated factor scores for each individual.

A logistic regression model with the backward elimination variable selection technique was then fitted with early glaucoma as the outcome variable and the estimated latent factor scores as candidate explanatory variables such that the probability of glaucoma for an individual is modeled using an exemplary Equation (1) below:

$$\log it[\text{Prob}(\text{Glaucoma})] = \beta_0 + \beta_1 * F1 + \ldots \beta_5 * F5 + \beta_6 * F1 * F2 + \ldots + \beta_{15} * F4 * F5, \quad (1)$$

where F1, F2, F3, F4, and F5 are the five estimated factor scores for an individual in the study (see Results section for more information on choice of five factors) and $\beta$ values are model coefficients.

From the estimated logistic regression coefficients, predicted probabilities for early glaucoma status along with 95% prediction intervals were calculated and submitted to a receiver operating characteristic (ROC) curve analysis. Cutoff points from the ROC plot were used to classify subjects based on predicted probabilities. Similar logistic regression and ROC curve analyses were carried out for single variable models and compared to the multivariable analysis.

The robustness of the models was validated in a separate set including 49 healthy subjects and 35 subjects with early glaucoma. Area under the curve (AUC) of the ROC, sensitivity, specificity, median 95% prediction interval length (PIL) of all prediction intervals, Akaike's information criterion (AIC), and classification rates were used to determine the performances of the models. Statistical analysis was performed with SAS version 9.2, available, for example, from SAS in Cary, N.C., with statistical significance level set at P less than 0.05.

Due to the complexity of the model, the statistical analysis involved, the factor scoring, and determining which variables of the 16 to combine as the most useful in predicting early onset glaucoma, it is apparent that the subject matter herein cannot be performed manually. Doctors cannot pick up a chart, examine 16 parameters, and mentally determine whether a patient has early onset glaucoma without computing technology. The subject matter herein is necessarily rooted in computing technology by virtue of utilizing a computing processor to execute a glaucoma predicting module for transformation of patient-specific data, including structural parameters measured via SD-OCT, upon application of a multivariable predictive model and aggregate patient dataset into a glaucoma prediction score for predicting and/or treating early onset glaucoma.

Results

The mean age in the modeling set was 66.0 6±11.85 years for patients with glaucoma and 62.8±9.47 years for healthy subjects (P=0.06). The mean age in the validation set was 67.9±12.56 years for patients with glaucoma and 61.7±9.56 years for healthy subjects (P=0.01). Since the groups differed statistically in terms of age in the validation set, the model controls for age of the subjects through use of a categorical age variable in the logistic regression models. The categories included, less than or equal to 57, 58 to 64, 65 to 72, and greater than 72, where approximately 25% of the sample was contained in each category. Controlling for age had little effect on the modeling results. The mean visual field MD of patients with glaucoma was −3.19±1.69 dB. All 16 structural parameters significantly differed between subjects with glaucoma and healthy subjects in both the modeling (all P≤0.001) and the validation set (all P<0.02).

EFA and Logistic Regression

Table 1, which, because of its size, is included as FIG. 1, and displays the sample correlation matrix produced by transforming patient data according to the exploratory factor analysis (EFA) method, which includes all 16 continuous variables in the analysis. The variables were scored so that a model trained using a smaller number of more predictive variables may be obtained. The estimated scoring coefficients from the EFA model needed to construct the latent factors are given in Table 2 below.

To calculate factor #j in Table 2 for an individual, the individual's original variables (standardized) are multiplied by the scoring coefficients for factor #1 and summed for each of the components. For example, factor #1=average GCIPL*(3.31)+minimum GCIPL*(0.07)+ . . . +CDR*(0.05)+VCDR*(−0.04). The estimated factor scores are then entered into the multiple logistic regression model and results are presented in Table 3. Note that only the first three factors are retained after implementing the backward elimination variable selection technique.

TABLE 2

Scoring Coefficients for the Variables in the Modeling Set

| Variables | Factor 1 | Factor 2 | Factor 3 | Factor 4 | Factor 5 |
|---|---|---|---|---|---|
| Average GCIPL | 3.31 | 0.23 | −0.32 | 0.62 | 0.71 |
| Minimum GCIPL | 0.07 | −0.02 | 0.01 | −0.04 | −0.04 |
| Superotemporal GCIPL | −0.37 | −0.05 | −0.08 | 0.06 | −0.01 |
| Superior GCIPL | −0.48 | −0.07 | −0.10 | 0.15 | 0.09 |
| Superonasal GCIPL | −0.36 | 0.04 | −0.16 | 0.09 | 0.04 |
| Inferonasal GCIPL | −0.42 | −0.03 | 0.11 | −0.22 | −0.21 |

TABLE 2-continued

Scoring Coefficients for the Variables in the Modeling Set

| Variables | Factor 1 | Factor 2 | Factor 3 | Factor 4 | Factor 5 |
|---|---|---|---|---|---|
| Inferior GCIPL | −0.36 | −0.02 | 0.24 | −0.42 | −0.35 |
| Inferotemporal GCIPL | −0.45 | −0.13 | 0.33 | −0.49 | −0.38 |
| Average RNFL | 0.46 | 0.06 | 1.29 | 3.20 | 3.81 |
| Temporal RNFL | −0.15 | −0.02 | −0.27 | 0.00 | −0.95 |
| Superior RNFL | −0.27 | 0.02 | −0.11 | −0.85 | −1.18 |
| Nasal RNFL | −0.10 | −0.01 | −0.23 | −0.61 | 0.06 |
| Inferior RNFL | −0.27 | −0.04 | 0.05 | −1.41 | −1.66 |
| Rim Area | 0.00 | −0.03 | 0.00 | −0.01 | 0.00 |
| CDR | 0.05 | 0.61 | −0.13 | −0.08 | −0.12 |
| VCDR | −0.04 | 0.35 | 0.19 | 0.10 | 0.12 |

EFA with promax rotation identified five latent factors, which explained a large proportion of the variability seen in the original set of 16 variables, in Table 3 below.

TABLE 3

Factor Loadings of the Variables in the Modeling Set

| Variables | Factor 1 | Factor 2 | Factor 3 | Factor 4 | Factor 5 |
|---|---|---|---|---|---|
| Average GCIPL | 0.892* | −0.006 | 0.104 | 0.070 | 0.021 |
| Minimum GCIPL | 0.867* | −0.127 | 0.086 | −0.052 | −0.052 |
| Superotemporal GCIPL | 0.786* | −0.063 | −0.062 | 0.232 | 0.097 |
| Superior GCIPL | 0.817* | 0.007 | −0.105 | 0.256 | 0.140 |
| Superonasal GCIPL | 0.906* | 0.077 | −0.152 | 0.212 | 0.144 |
| Inferonasal GCIPL | 0.877* | 0.044 | 0.138 | −0.002 | −0.039 |
| Inferior GCIPL | 0.808* | −0.021 | 0.328 | −0.140 | −0.128 |
| Inferotemporal GCIPL | 0.682* | −0.085 | 0.413 | −0.160 | −0.102 |
| Average RNFL | 0.079 | −0.034 | 0.695* | 0.294 | 0.211 |
| Temporal RNFL | 0.132 | −0.101 | 0.216 | 0.824* | −0.352 |
| Superior RNFL | 0.062 | 0.047 | 0.647* | 0.328 | 0.208 |
| Nasal RNFL | 0.044 | −0.051 | 0.154 | −0.297 | 0.963* |
| Inferior RNFL | 0.045 | −0.038 | 0.856* | −0.074 | 0.055 |
| Rim area | 0.122 | −0.439* | 0.368 | 0.066 | 0.103 |
| CDR | 0.000 | 1.004* | 0.053 | −0.033 | −0.031 |
| VCDR | −0.003 | 0.951* | −0.035 | −0.037 | −0.002 |

*Denote loaded factors (>0.43 or <−0.43).

Using the oblique promax rotation results in factor loadings that are no longer correlation coefficients, but instead represent regression coefficients that are not confined between −1 and 1. [19]

Figure 3:
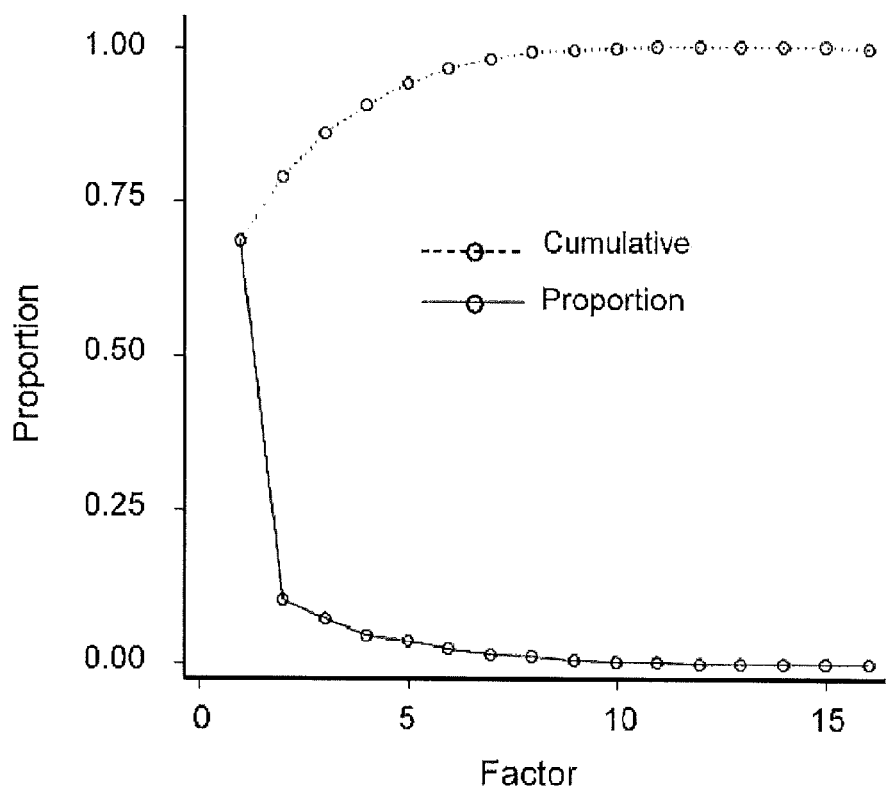
FIG. 3 is a graphical illustration of the proportion or factor of variance associated with the structural parameters as measured using SD-OCT.

The choice to retain five factors was made based on the scree plot (i.e., a graphical display of the variance of each component in the dataset) of eigenvalues and analysis of accounted for variance. The scree plot of the 16 variables is shown in FIGS. 2 and 3, the proportion of accounted for variance for each factor is displayed along with the cumulative proportions. FIG. 2 is a scree plot of eigenvalues from the EFA and FIG. 3 is the proportion of variance explained by each identified factor with cumulative proportions.

The factor loadings, which reflect on the relative weights of the variable in the component, indicated that factor #1 was dominated by all GCIPL variables, factor #2 by all three ONH parameters, factor #3 by average, superior, and inferior quadrant RNFL, factor #4 by temporal RNFL, and factor #5 by nasal RNFL. Factors #1 and #3 through #5 each weighted positively on their respective variables while factor #2 had positive loadings for CDR and VCDR but a negative loading on rim area.

This indicates that factor #2 represents the contrast between CDR/VCDR and rim area. The cutoff point of 0.43 used in Table 3 above is based on simulation studies carried out by Hair et al., [20] that considered sample size, a power level of 0.80, and level of significance of 0.05. These five factors combined accounted for 94.18% of the variability seen in the original set of 16 variables, greatly reducing the number of variables in the multiple logistic regression analysis while maintaining a majority of the available information.

The results of logistic regression with backward elimination in the modeling set that included early glaucoma status as the dependent variable and these five estimated factor scores as predictors (along with their first order interactions), calculated for each subject, identified factor #1, factor #2, and factor #3 (Table 4) as statistically significant predictors of glaucoma, with an AIC of 43.29 (Table 5, FIG. 4). Table 4 is below and indicates variable selection by logistic regression with backward elimination for the modeling set. Table 5, because of its size, is included as FIG. 4 and indicates the discriminating ability of the multivariable and single variable analyses in the modeling set, and proportion of subjects correctly classified and median length of prediction intervals in the validation set.

TABLE 4

Variable Selection by Logistic Regression With Backward Elimination for the Modeling Set*

| Variables | Estimate | P |
|---|---|---|
| Intercept | −2.410 | 0.0075 |
| Factor 1: all GCIPL | −2.685 | 0.0116 |
| Factor 2: all ONH | 7.307 | 0.0036 |
| Factor 3: RNFL subset | −3.344 | 0.0044 |

*Performed after controlling for age of the subjects.

The results in Table 3 above indicate that an increase in an individual's score for factor #2 leads to an increase in the probability of glaucoma, implying that as the difference between of CDR/VCDR and rim area measurements increases, the probability of glaucoma increases. In addition, the results confirm that as the GCIPL and RNFL factor scores increase, the probability of glaucoma decreases.

Figure 5:
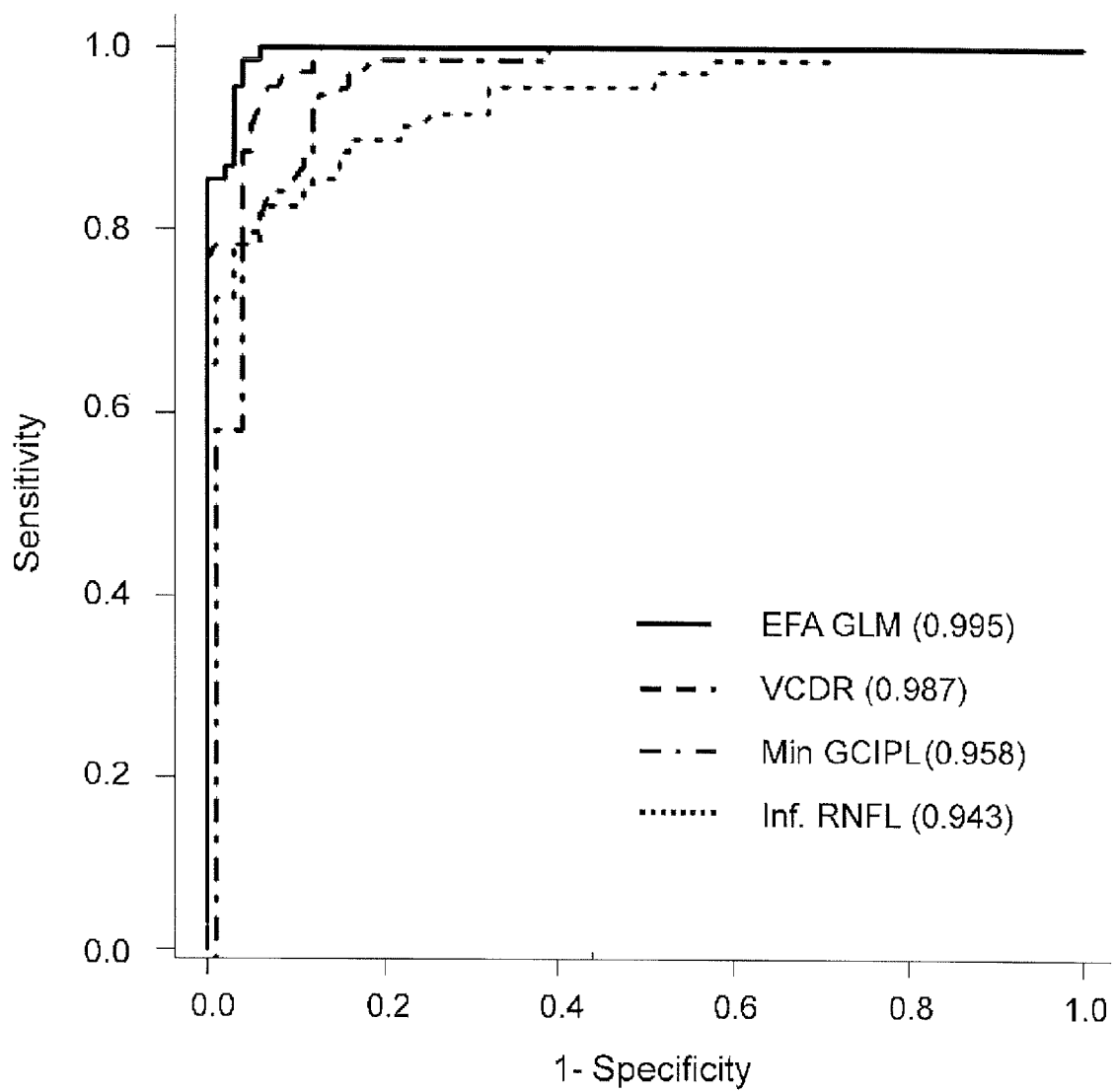
FIG. 5 is a graphical illustration of receiver operating characteristic (ROC) curves comparing univariable and multivariable logistic regression models generated using structural parameter as measured using SD-OCT.

Table 5 in FIG. 4 shows that the AUC and sensitivity at fixed levels of specificity of the multivariable model was slightly higher than corresponding values of the best three single variables, while the AIC significantly improved from 113.16 to 59.64 to 43.29 in the univariable and multivariable models, respectively. Differences of four or more in AIC indicate that the lower valued model is preferred. [21] The AUC value for the multivariable model is also shown to be significantly larger than each of the single variable models at the 0.10 level of significance. The results are based on a nonparametric statistical test, which compares the areas under correlated ROC curves and is available in SAS version 9.2. [22] FIG. 5 displays the ROC curves for all of the considered models in the analysis of the modeling set.

The multivariable model applied in a blinded manner to a separate set of healthy subjects and subjects with early glaucoma (validation set) produced another significant discriminant function that correctly classified 91.67%, compared with 80.95% to 90.48% for single variables (see, Table 5). The multivariable PILs were 1.9 to 3.0 times narrower on average than those of single variable models, indicating that it would be easier to predict the status of a subject using the multivariable rather than a univariable model by correctly characterizing the uncertainty associated with the predictions.

II. Glaucoma Prediction

Discussion

Methods, system, and computer readable media herein utilize a classification method including generation of a prediction score or glaucoma probability score used for early glaucoma. The perdition score is developed on EFA followed by logistic regression of constructed glaucomatous structural parameters measured with SD-OCT. The method is designed on the assumption that a method combining structural parameters from ONH, RNFL, and GCIPL may improve the discrimination between eyes with early glaucoma and healthy eyes.

With the availability of various imaging devices that provide quantitative evaluation of structural parameters, the number of parameters has increased significantly, making the interpretation more difficult. The multivariate analysis described herein produced a better predictive model than the univariable analysis. The multivariate analysis was achieved by combining OCT structural parameters in a weighted (transformed) manner that was dictated by the data rather than an arbitrary combination. This weighting was done through two sequential methods: (1) EFA, which combined the OCT ONH, RNFL, and GCIPL measures into factor scores that represented a variable's performance more parsimoniously and with greater interpretability, and (2) multiple logistic regression modeling, which selected and weighted the factor scores with the greatest power to differentiate patients with early glaucoma from healthy subjects. Methods, system, and computer readable media herein confirmed that the OCT measures are sensitive to group differences between early-stage glaucoma and normal state.

Significant effort has been invested in reducing the number of parameters through combinations that will increase glaucoma diagnostic accuracy. In this perspective, studies have used combination of parameters obtained with different devices (i.e., SLO and SLP or SLO and OCT) [8, 11, 12] or parameters derived from one device (i.e., SLO or OCT). [10, 14, 23-26] Badala et al. [8] used a classification and regression tree analysis (CART) to compare early glaucoma diagnostic performance of individual parameters with time domain OCT, SLP, SLO, and qualitative assessment of optic disc photographs and their combinations. No significant difference was found between individual best parameters from the four methods, but the combination of time domain OCT average RNFL thickness and SLO-based CDR resulted in a good diagnostic precision (93%), sensitivity (91%), and specificity (96%).

The ability of SLP and SLO parameters to discriminate between healthy and glaucomatous eyes was also investigated by Magacho et al. [11] using multivariate discriminant formulas for each device individually and for both devices combined. The combination of parameters resulted in higher sensitivity, specificity, and accuracy compared with individual parameters on each device. Similarly, combining parameters of both devices achieved higher performances compared with combination of parameters of either device.

Using the or-Logic combination of criteria from SLO and SLP, Toth et al. [12] reported that combining various SLP criteria improved the accuracy and positive likelihood ratio (PLR) for early glaucoma. No improvement was observed following combination of SLO-based criteria alone; however, combining the best SLP and SLO criteria increased the PLR compared with combinations of SLO criteria alone, but decreased the PLR of SLP combination criteria.

The or-Logic combination approach was also investigated by Budenz et al. [23] and in the Advanced Imaging Glaucoma Study (AIGS) [25] using time domain OCT derived RNFL criteria. In the former study, the combination of one or more abnormal quadrants or clock hours and abnormal average RNFL at less than 5% level provided the best sensitivity for the diagnosis of glaucoma. However, AUCs for those combinations were not provided so that it was unclear what the best combinations were. In the latter study, the combination of average, inferior, and superior quadrant RNFL yielded an AUC of 0.92 compared with best single parameter (0.89).

In a subsequent investigation, the AIGS [26] evaluated the performance of the or-Logic combination, support vector machine, relevance vector machine, and LDF methods using time domain OCT ONH, RNFL, and macular variables. The AUCs of the combination of the best three RNFL variables (inferior quadrant, overall average, and superior quadrant RNFL) with the best three ONH variables (horizontal integrated rim width, vertical integrated rim area, and VCDR) were similar (0.943-0.954), but greater than those of the overall best single parameter. However, in both AGISs, the study populations included all severity stages of glaucoma and no separate analysis was performed or provided for early glaucoma.

Medeiros et al. [9] also showed that the PCA followed by LDF combining time domain OCT average, RNFL at 7 o'clock, and RNFL at 11 o'clock with VCDR achieved a significantly larger AUC of 0.97 than that 0.91 for best single parameter.

Other studies have assessed the diagnostic performance SLO-based optic disc parameters individually and in combination oftentimes using pre-established LDF or machine learning classifiers. One of these studies compared the diagnostic performances of three LDFs (Bathija's, [27] Mikelberg's, [28] and Burk's [29]) and the Moorfields Regression Analysis. At fixed specificity of 95%, these four methods had comparable low sensitivities that did not exceed 60%. [10]

In another study the LDF from stepwise linear regression of SLO optic disc parameters had a sensitivity of 74.2% compared with SLO built-in LDFs (70.4% for Mikelberg's and 67.6% for Burk's) at fixed specificity of 85%. 30 The study by Lester et al. [31] compared the ability for early detection of glaucomatous optic disc by five formulas: Bathija's, [27] Mikelberg's, [28] Mardin's, [32] the sector based LDF by Lester et al., [33] and the CSLO-based cup shape measure. The optic disc sector-based LDF outperformed the other formulas, with single cup shape measure having the lowest performance. The same formulas, except Mardin's, were used in a subsequent study by the same investigators to compare their ability to detect glaucomatous visual field defects. [24] The results confirmed their previous finding that the optic disc-based sector LDF and the cup shape measure were the best and worst formulas, respectively. [31] Because SLO based LDFs rely on manual outlining of the optic disc contour, these methods are likely to be affected by the interobserver variability.

Unlike earlier studies that used SLO, SPL, and time-domain OCT, two recent studies have reported on the diagnostic performance of combined ONH, peripapillary RNFL, GCC parameters measured with SD-OCT (e.g., RTVue-100 available from Optovue, Fremont, Calif.). Vertical cup-to-disc diameter ratio, average RNFL thickness, and average GCC thickness area provided the best AUCs for discriminating between healthy subjects and subjects with perimetric glaucoma, [14] or for discriminating between glaucoma suspects and subjects with definite glaucoma. [15]

The combination of parameters resulted in increased diagnostic performance in both studies, but the resulting LDFs did not include any of the ganglion cell layer variables. Anatomically, the GCC is made of the RNFL and ganglion cell layer, and the inner plexiform layer. Thus, combining GCC and RNFL parameters is somewhat flawed because the GCC already contains the RNFL, and it is not clear how this may have affected the linear discriminant analysis. Combination of Cirrus HD-OCT (e.g., available from Carl Zeiss Meditec, Inc.) structural parameters was recently shown to enhance significantly discrimination between healthy subjects and subjects with mild glaucoma using both linear discriminant analysis and CART. [13] However, this study did not include the GCIPL in the combination. To date, there has not been another study that assessed the diagnostic ability of combined ONH, RNFL, and GCIPL parameters.

Methods and systems herein only included patients with early glaucoma because it is oftentimes hard to distinguish early stages of the disease and normal state. This may be a limitation of this study. Indeed, using a group of patients at all stages of disease severity in the development of the underlying structure would tend to avoid restricting the range in the test measures and therefore attenuating correlations among variables that can result in falsely low estimates of factor loadings. [34]

In contrast to our study, most previous studies [9-12, 23-26, 30, 31] included patients with all spectra of glaucoma severity, but did not provide the diagnostic performance for early glaucoma. Because the performance of glaucoma diagnostic devices is often dependent on disease severity, the glaucoma performances reported in those studies would have been lower if the analysis was restricted to early glaucoma. Methods and systems herein also differ from earlier studies [9, 35] in that EFA rather than principal component analysis (PCA) was performed prior to logistic regression.

PCA is only a data reduction method and it is computed without regard to any underlying structure influenced by latent variables. In addition, in PCA, components are calculated using all of the variance of the manifest variables, so that the whole variance appears in the solution. PCA does not discriminate between shared and unique variance. [36] On the contrary, EFA reveals latent variables that possibly cause the manifest variables to covary. During factor extraction the shared variance of a variable is partitioned from its unique variance and error variance to reveal the underlying factor structure; only shared variance appears in the solution. If the factors are uncorrelated and communalities are moderate, it tends to overestimate values of variance accounted for by the components. Since EFA only considers shared variance, it should yield similar results while also avoiding the inflation of estimates of variance accounted for. [37, 38]

Methods and systems used herein, namely sequentially combining EFA and logistic regression modeling, benefited from several advantages. First, the use of EFA reorganizes a large amount of data into a more parsimonious set of component scores. Because each EFA component groups together correlated test measures, the component scores more directly gauge a variable's performance with regard to glaucoma status. Second, because the component structure was created via transforming from the data of both glaucoma and control subjects, the component structure reflects the structural differences between the two groups as well as the differences among subjects within each group. Third, the discriminant function weights the components in terms of their contributions to discriminating patients with early glaucoma from controls and then classifies each individual with high accuracy, sensitivity, and specificity. Fourth, methods and systems herein go beyond simple calculation of AUC, sensitivity and specificity by providing AIC, and most importantly the predicted probability of early glaucoma for an individual along with a 95% prediction interval, which may prove extremely useful and influence the physician's decision to initiate treatment.

Despite only slight increase in AUC, the AIC and PIL of the multivariable model were significantly lower than those of the three best single parameters models (Table 5, FIG. 4), indicating that the multivariable predictive model described herein performs better and is more accurate than univariable models both at detecting the disease and differentiating between affected and unaffected individuals.

An additional difference to consider is that most prior studies did not validate their discriminant functions in separate set of subjects. Validation ensures that the proposed model is robust to the subjects included in the analysis and will be useful for analyzing and/or transforming data from future datasets into an accurate early onset glaucoma predictor.

Fifth, both the modeling and validation sets were drawn from the same sample selected with same inclusion and exclusion criteria. It is unclear whether this affected the performance of the model. Not having performed visual field in healthy subjects may be another methodological limitation of this study.

Indeed, relying on IOP measurement and the ophthalmoscopic appearance of the optic disc as assessed by fellowship-trained glaucoma subspecialists may not have been sufficient to confidently exclude all subjects with glaucoma among normal subjects. This is particularly true in subjects with early stages of glaucoma where functional deficits may precede detectable structural changes. Whether some glaucoma patients were missed among healthy subjects and whether this may have affected our results in a significant manner is unknown.

On the other hand, the diagnostic performance of the instant model described herein may have been inflated to some extent as a result of studying two clinically well-defined populations, namely non-glaucomatous and glaucomatous subjects. Therefore, further work may include evaluating the diagnostic performance of this model in subjects suspected of having glaucoma. Doing so will both comply with the general principle that a diagnostic test is useful if it can decrease or eliminate the uncertainty with respect to the diagnosis (i.e., in glaucoma suspects) or to the disease stage and determine the "true" diagnostic performance of this model.

Methods, systems, and computer readable media described herein provide a model based on the sequential partnering of EFA and multiple logistic regressions of SD-OCT structural parameters. This produced improved results in both the modeling and the validation sets. The model was successful in predicting early glaucoma status and outperformed univariable models in terms AIC, median PILs, and classification rates. The classification method based on EFA of structural parameters described herein is a robust and powerful method for the diagnosis of early glaucoma. It may become a valuable part of the toolbox of discriminatory analysis.

Figure 6:
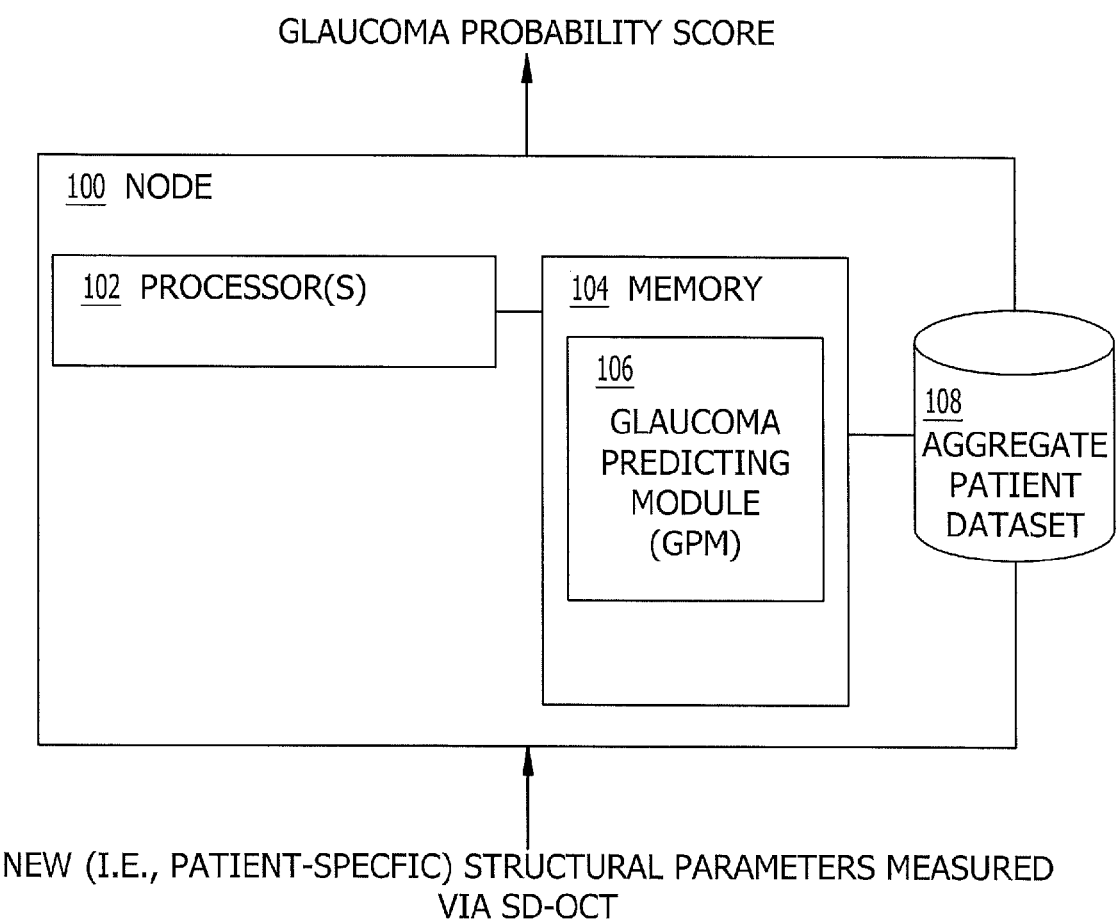
FIG. 6 is a block diagram of an exemplary system for predicting early onset glaucoma according to an embodiment of the subject matter described herein.

FIG. 6 is a block diagram illustrating an exemplary system or node 100 (e.g., a single or multiple processing core computing device or computing platform) configured to predict early onset glaucoma, or a patient's percentage or probability (i.e., from between approximately 0 and 100%) of having early onset glaucoma. Node 100 may include any suitable entity, such as a computing device or computing platform for performing one more aspects of the present subject matter described herein or in the publication entitled "Combining Spectral Domain Optical Coherence Tomography Structural Parameters for the Diagnosis of Glaucoma with Early Visual Field Loss", as published in *Invest Ophthalmol Vis Sci*. 2013; 54:8393-8400. DOI:10.1167/iovs.13-12749, the disclosure of which is incorporated herein by reference in its entirety.

In accordance with embodiments of the subject matter described herein, components, modules, and/or portions of node 100 may be implemented or distributed across one or more (e.g., multiple) devices or computing platforms. For example, a cluster of nodes 100 may be used to perform various portions or steps associated with glaucoma prediction.

It should be noted that node 100 and its components and functionality described herein constitute a special purpose test node or computing device that improves the technological field of OCT by allowing prediction of early onset glaucoma via structural parameters before a perceptible loss in vision or ocular function occurs, thereby preventing irreversible blindness. Functionality of node 100 cannot be performed manually, as it is necessarily rooted on computing technology by virtue of utilizing a computing processor to execute a glaucoma predicting module for transformation of patient-specific data, including structural parameters measured via SD-OCT, upon application of a multivariable predictive model and aggregate patient dataset into a glaucoma prediction score for predicting and/or treating early onset glaucoma.

In some embodiments, node 100 includes a computing platform that includes one or more processors 102. In some embodiments, processor 102 includes a hardware processor, a multi-core processor, or any suitable other processing core, including processors for virtual machines, adapted to execute instructions stored by an access memory 104.

Memory 104 may include any non-transitory computer readable medium and may be operative to communicate with one or more of processors 102. Memory 104 may include glaucoma predicting module (GPM) 106. In accordance with embodiments of the subject matter described herein, GPM 106 may be configured to obtain and/or receive structural parameter values (e.g., measured using SD-OCT) associated with a new patient, standardize the patient-specific values via a modeling dataset or aggregate patient data (i.e., an aggregate patient dataset) stored in a database 108 or other storage module. For example and as illustrated in Tables 6-8 below, individual patient GCIPL, RNFL, and ONH data can be received and standardized using means and standard deviations calculated for variables stored in a data set or database 108.

GPM 106 is further configured to generate and/or calculate as output, a glaucoma probability score ($p_i$) for a new patient (i.e., for which the patient-specific data was obtained) based upon a multivariable predictive model stored within GPM 106 and/or accessed thereby, which scores, as input, the structural data of the new patient using coefficients obtained or calculated from data in database 108. The glaucoma probability score may be calculated from an equation similar to Equation (2) below:

$$p_i = 1 / \left[ 1 + \exp \left\{ \begin{array}{l} -[\beta_0 + \beta_1 F_1 + \beta_2 F_2 + \\ \beta_3 F_3 + \beta_4 F_1 F_3 + \\ \beta_5 I(\text{Age}_i \text{ in Category 1}) + \\ \beta_6 I(\text{Age}_i \text{ in Category 2}) + \\ \beta_7 I(\text{Age}_i \text{ in Category 3})] \end{array} \right\} \right]$$

Equation (2)

The predictive equations may change some based upon the data set 108, as new data is continuously updated and/or added, however, the method of arriving at and/or transforming data upon applying the multivariable predictive model is the same. In the equation above, factors F1 to F5 are calculated from an individual patient's factors, for example, via an EFA method applied to the 16 structural parameters obtained via SD-OCT. The β values are coefficients of the logistic regression model. Sample β values are applied to patient data in Tables 6-13 below. Processor 102 may predict, and transmit as output, a glaucoma prediction score via GPM 106. The glaucoma prediction score is a number between 0 and 1, which indicates a patients probability or percentage of having glaucoma (i.e., between 0% and 100%.). The physician may use this information in providing patient care, and to decide what further testing/treatments may be needed, if any.

In some embodiments, node 100 is a special purpose computer that predicts glaucoma and obviates the need for a patient to experience perceptible visual field loss, irreversible blindness, and/or a loss in ocular function by determining that a patient has early onset glaucoma (i.e., as opposed to later stages of glaucoma coincident with loss in vision and/or vision field loss). Thus, node 100 is beneficial in preventing vision loss by inputting patient-specific data, transforming the data into an indicator of early onset glaucoma, and outputting the indicator for use in further testing and/or treatment, if further testing and/or treatment is necessary. Node 100 is configured to generate a probability score upon analyzing and transforming patient-specific structural data obtained via SD-OCT. This is advantageous, as a patient's chances of significant visual field loss can be preempted.

In some embodiments, GPM 106 is configured to implement EFA, which combines a patient's OCT measurements, for example, ONH, RNFL, and GCIPL measurements into factor scores that represented a variable's performance and a multiple logistic regression model, which selects and weights the factor scores with the greatest power to differentiate patients with early glaucoma from healthy subjects. Exemplary modeling techniques are described herein may be used, executed, and/or implemented by GPM 106.

In accordance with embodiments of the subject matter described herein, GPM 106 may be configured to work in parallel with a plurality of processors (e.g., processors 102) and/or other nodes. For example, a plurality of processor cores may each be associated with implementing EFA for different OCT measurements.

It will be appreciated that FIG. 6 is for illustrative purposes and that various components, their locations, and/ or their functions may be changed, altered, added, or removed. For example, components and/or functions may be combined into a single entity. In a second example, a node and/or function may be located at or implemented by two or more nodes.

Figure 7:
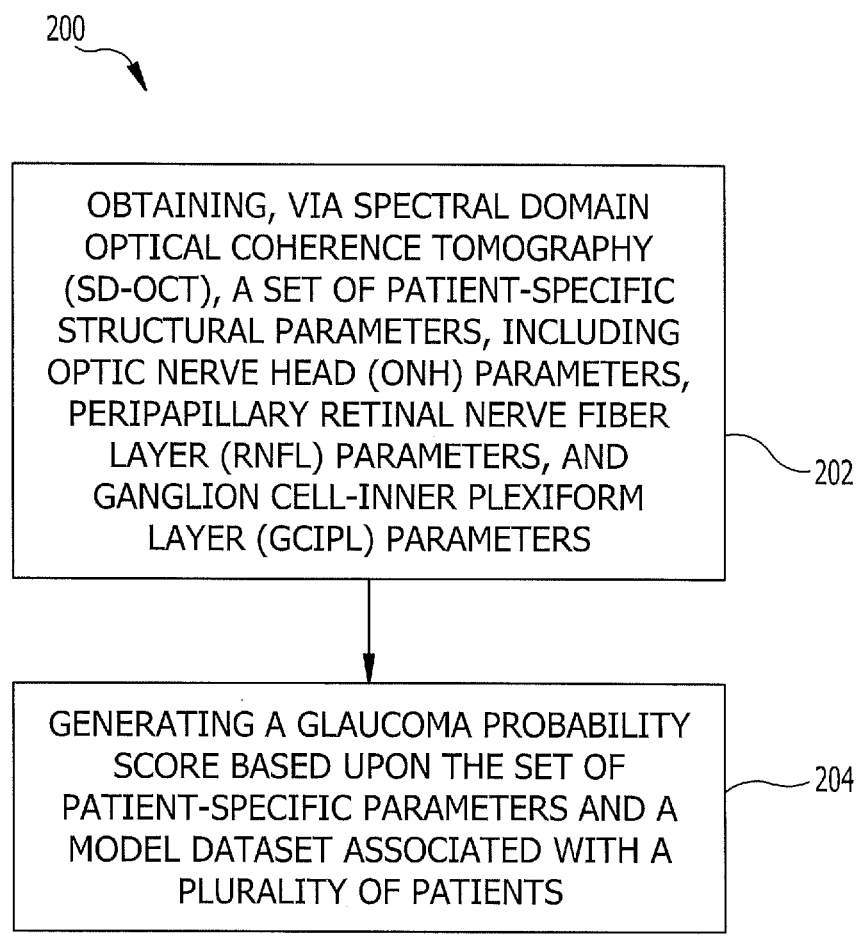
FIG. 7 is a block diagram illustrating an exemplary method for predicting early onset glaucoma according to an embodiment of the subject matter described herein.

FIG. 7 is a block diagram illustrating an exemplary method, generally designated 200, of predicting whether a patient has early onset glaucoma using patient-specific structural data obtained via SD-OCT and transforming the patient-specific data into a glaucoma probability score via application of a multivariable predictive model generated from an aggregate patient dataset for a plurality of patients. At block 202, a set of patient-specific structural parameters is measured or obtained using SD-OCT. The patient-specific structural parameters may include ONH, peripapillary RNFL, and macular GCIPL parameters. At block 204, a glaucoma probability score is generated based upon incorporating/analyzing and/or otherwise transforming patient-specific parameters via application of a prediction model calculated from a modeling dataset including data for a plurality of patients. The glaucoma probability score predicts a given patient's probability or chance of having early onset glaucoma from between approximately 0 and 100%. The probability score may be used for treating a patient, where necessary.

III. Exemplary Prediction for New Patients Via Model

In the exemplary predicted probability calculations, the formulas are slightly different from that in Equation (1) above. The formulas have changed due to changes in the dataset being analyzed. When arriving at Equation 1, the full dataset was divided into a modeling dataset (⅔ of the original size) and a validation dataset (⅓ of the original size). This was done so that we could validate our model.

In the version of the exemplary model herein however, both datasets are combined in order to increase the sample size and improve the estimation of the unknown model parameters. The formulas are expected to further change and/or become refined in the future due to the inclusion of more participants and possibly new variables as well. However, the method for calculating predicted probabilities remains the same across all datasets.

Predicted probabilities are calculated for two patients who were not included in the full analysis dataset and who have unknown true glaucoma status (Table 1-Table 8). For these individuals the true glaucoma status was known, and was also predicted for determining how well the model did at predicting the outcome in comparison with the best fitting single variable model. (Patient GS01 did not have glaucoma, and patient GS09 did have glaucoma).

The treating physician designated these patients as "glaucoma suspects", meaning despite all the information at his disposal, the physician could not say whether the patients were normal or had glaucoma.

Glaucoma is a chronic degenerative disease of the optic nerve that leads to blindness if left untreated. Early diagnosis allows early treatment that delays significantly the progression of the disease. The diagnosis of glaucoma in early stages is oftentimes difficult even for the glaucoma specialist. Thousands of people are wrongly diagnosed has having glaucoma every year and unnecessarily put on lifelong treatment. Conversely, others a let untreated for some time because the disease cannot be diagnosed with certainty; in the meantime, the disease progresses silently in the background. The bad news with glaucoma is that the vision that is lost is gone forever and will not come back even after treatment is started. The role of the treatment is to prevent further deterioration of vision and preserve what is left at the time of diagnosis.

In a first step, the observed, measured, and/or obtained values for each patient are standardized. Table 6 below illustrates calculation of means/standard deviations of variables from the full analysis data set. Table 7 is the patient specific non-standardized information, and Table 8 is standardized data for each patient (i.e., patient specific data of Table 7 is standardized according to full analysis dataset values of Table 6).

TABLE 6

MEANS AND STANDARD DEVIATIONS OF VARIABLES FROM THE FULL ANALYSIS DATASET

| Variable | Mean | Std Dev |
| --- | --- | --- |
| AVRG_GCIPL | 75.03557 | 10.22343 |
| MIN_GCIPL | 70.78261 | 13.21180 |
| SUPTEM_GCIPL | 75.01186 | 10.33621 |
| SUP_GCIPL | 76.53360 | 11.34225 |
| SUPNAS_GCIPL | 77.37154 | 11.13251 |
| INFNAS_GCIPL | 74.57708 | 10.61702 |
| INF_GCIPL | 72.30435 | 11.34306 |
| INFTEMP_GCIPL | 73.97628 | 11.36652 |
| AVRG_RNFL | 81.41897 | 14.40177 |
| TEMP_RNFL | 58.86957 | 13.09591 |
| SUP_RNFL | 100.31621 | 21.53907 |
| NAS_RNFL | 65.11067 | 10.97958 |
| INF_RNFL | 101.44664 | 25.25383 |
| RIM_AREA | 1.09336 | 0.33601 |
| CDR | 0.59309 | 0.18324 |
| VCDR | 0.57680 | 0.19264 |

TABLE 7

ORIGINAL (UNSTANDARDIZED) INFORMATION FOR TWO PATIENTS NOT INCLUDED IN FULL ANALYSIS DATASET

| Variable | Person GS01, OD | Person GS09, OD |
| --- | --- | --- |
| AVRG_GCIPL | 74 | 66 |
| MIN_GCIPL | 67 | 52 |
| SUPTEM_GCIPL | 80 | 76 |
| SUP_GCIPL | 82 | 62 |
| SUPNAS_GCIPL | 70 | 53 |
| INFNAS_GCIPL | 68 | 58 |
| INF_GCIPL | 72 | 66 |
| INFTEMP_GCIPL | 73 | 78 |
| AVRG_RNFL | 69 | 63 |
| TEMP_RNFL | 52 | 42 |
| SUP_RNFL | 72 | 71 |
| NAS_RNFL | 50 | 62 |
| INF_RNFL | 104 | 78 |
| RIM_AREA | 1.36 | 0.68 |
| CDR | 0.60 | 0.81 |
| VCDR | 0.54 | 0.80 |

TABLE 8

STANDARDIZED INFORMATION FOR THE TWO PATIENTS

| Variable | Person GS01, OD | Person GS09, OD |
| --- | --- | --- |
| AVRG_GCIPL | (74 − 75.03557)/10.22343 = −0.1012938 | (66 − 75.03557)/10.22343 = −0.88381 |
| MIN_GCIPL | (67 − 70.78261)/13.21180 = −0.2863054 | (52 − 70.78261)/13.21180 = −1.421654 |
| SUPTEM_GCIPL | (80 − 75.01186)/10.33621 = 0.4825889 | (76 − 75.01186)/10.33621 = 0.09559984 |
| SUP_GCIPL | (82 − 76.53360)/11.34225 = 0.4819502 | (62 − 76.53360)/11.34225 = −1.281368 |

TABLE 8-continued

STANDARDIZED INFORMATION FOR THE TWO PATIENTS

| Variable | Person GS01, OD | Person GS09, OD |
|---|---|---|
| SUPNAS_GCIPL | (70 − 77.37154)/11.13251 = −0.6621633 | (53 − 77.37154)/11.13251 = −2.189222 |
| INFNAS_GCIPL | (68 − 74.57708)/10.61702 = −0.6194846 | (58 − 74.57708)/10.61702 = −1.561368 |
| INF_GCIPL | (72 − 72.30435)/11.34306 = −0.02683138 | (66 − 72.30435)/11.34306 = −0.5557892 |
| INFTEMP_GCIPL | (73 − 73.97628)/11.36652 = −0.08589084 | (78 − 73.97628)/11.36652 = 0.3539975 |
| AVRG_RNFL | (69 − 81.41897)/14.40177 = −0.8623225 | (63 − 81.41897)/14.40177 = −1.278938 |
| TEMP_RNFL | (52 − 58.86957)/13.09591 = −0.5245584 | (42 − 58.86957)/13.09591 = −1.288156 |
| SUP_RNFL | (72 − 100.31621)/21.53907 = −1.314644 | (71 − 100.31621)/21.53907 = −1.361071 |
| NAS_RNFL | (50 − 65.11067)/10.97958 = −1.376252 | (62 − 65.11067)/10.97958 = −0.2833141 |
| INF_RNFL | (104 − 101.44664)/25.25383 = 0.1011078 | (78 − 101.44664)/25.25383 = −0.928439 |
| RIM_AREA | (1.36 − 1.09336)/0.33601 = 0.7935478 | (0.68 − 1.09336)/0.33601 = −1.230201 |
| CDR | (0.60 − 0.59309)/0.18324 = 0.03771011 | (0.81 − 0.59309)/0.18324 = 1.183748 |
| VCDR | (0.54 − 0.57680)/0.19264 = −0.1910299 | (0.80 − 0.57680)/0.19264 = 1.158638 |

In a second step, the data (standardized patient data, Table 8) is scored using the standardized scoring coefficients. Table 9 below contains the standardized scoring coefficients or factor scores that represent a variable's performance within the full data set, and Table 10 below is the scored patient specific data, which results in calculation of the first factor (i.e., Factor 1).

TABLE 9

Standardized Scoring Coefficients

| | Factor 1 | Factor 2 | Factor 3 | Factor 4 | Factor 5 |
|---|---|---|---|---|---|
| AVRG_GCIPL | 3.26106098 | 0.18783633 | −0.7392737 | 1.02122413 | 0.82385304 |
| MIN_GCIPL | 0.04978323 | −0.0192653 | 0.01351416 | −0.0344963 | −0.029973 |
| SUPTEM_GCIPL | −0.3902494 | −0.0402528 | 0.01548565 | −0.0102909 | −0.0663142 |
| SUP_GCIPL | −0.4525977 | −0.0662637 | −0.0198481 | 0.10382726 | 0.05123997 |
| SUPNAS_GCIPL | −0.3544955 | 0.04410027 | −0.1481583 | 0.05667214 | 0.02358256 |
| INFNAS_GCIPL | −0.3819921 | −0.028891 | 0.11857505 | −0.2150374 | −0.1544252 |
| INF_GCIPL | −0.3513102 | 0.00012982 | 0.28299454 | −0.5077073 | −0.342163 |
| INFTEMP_GCIPL | −0.4080233 | −0.0985681 | 0.41813544 | −0.5731262 | −0.3745102 |
| AVRG_RNFL | 0.03694722 | 0.15958235 | 1.39798822 | 3.15514743 | 4.0154509 |
| TEMP_RNFL | −0.0631978 | −0.0447939 | −0.2846378 | 0.00462637 | −0.9752696 |
| SUP_RNFL | −0.1062269 | −0.0356947 | −0.0948571 | −0.8546236 | −1.3357344 |
| NAS_RNFL | −0.0169955 | −0.0282547 | −0.2300863 | −0.576664 | 0.11194432 |
| INF_RNFL | −0.0751923 | −0.086416 | 0.04689793 | −1.4469924 | −1.7628412 |
| RIM_AREA | 0.00084119 | −0.0343892 | −0.00485 | −0.0025921 | 0.00547889 |
| CDR | 0.05285721 | 0.61912554 | −0.1496886 | −0.0350845 | −0.0667175 |
| VCDR | −0.0540561 | 0.33546894 | 0.21666665 | 0.06131971 | 0.07639571 |

TABLE 10

Creating Factor 1 for Each of the Patients Not Included in the Full Analysis Dataset. Factors 2-5 Can be Created in a Similar Way

| Variable | Person GS01, OD | Person GS09, OD |
|---|---|---|
| AVRG_GCIPL | −0.1012938 × 3.26106098 = −0.3303253 | −0.88381 × 3.26106098 = −2.882158305 |
| MIN_GCIPL | −0.2863054 × 0.04978323 = −0.01425321 | −1.421654 × 0.04978323 = −0.070774528 |
| SUPTEM_GCIPL | 0.4825889 × −0.3902494 = −0.18833 | 0.09559984 × −0.3902494 = −0.037307780 |
| SUP_GCIPL | 0.4819502 × −0.4525977 = −0.2181296 | −1.281368 × −0.4525977 = 0.579944210 |
| SUPNAS_GCIPL | −0.6621633 × −0.3544955 = 0.2347339 | −2.189222 × −0.3544955 = 0.776069348 |

TABLE 10-continued

Creating Factor 1 for Each of the Patients Not Included in the Full Analysis Dataset. Factors 2-5 Can be Created in a Similar Way

| Variable | Person GS01, OD | Person GS09, OD |
| --- | --- | --- |
| INFNAS_GCIPL | −0.6194846 × −0.3819921 = 0.2366382 | −1.561368 × −0.3819921 = 0.596430241 |
| INF_GCIPL | −0.02683138 × −0.3513102 = 0.009426137 | −0.5557892 × −0.3513102 = 0.195254415 |
| INFTEMP_GCIPL | −0.08589084 × −0.4080233 = 0.03504546 | 0.3539975 × −0.4080233 = −0.144439228 |
| AVRG_RNFL | −0.8623225 × 0.03694722 = −0.03186042 | −1.278938 × 0.03694722 = −0.047253204 |
| TEMP_RNFL | −0.5245584 × −0.0631978 = 0.03315094 | −1.288156 × −0.0631978 = 0.081408625 |
| SUP_RNFL | −1.314644 × −0.1062269 = 0.1396506 | −1.361071 × −0.1062269 = 0.144582353 |
| NAS_RNFL | −1.376252 × −0.0169955 = 0.02339009 | −0.2833141 × −0.0169955 = 0.004815065 |
| INF_RNFL | 0.1011078 × −0.0751923 = −0.007602528 | −0.928439 × −0.0751923 = 0.069811464 |
| RIM_AREA | 0.7935478 × 0.00084119 = 0.0006675245 | −1.230201 × 0.00084119 = −0.001034833 |
| CDR | 0.03771011 × 0.05285721 = 0.001993251 | 1.183748 × 0.05285721 = 0.062569617 |
| VCDR | −0.1910299 × −0.0540561 = 0.01032633 | 1.158638 × −0.0540561 = −0.062631452 |
| Sum (Factor 1): | −0.06547857 | −0.734714 |

Table 10 above illustrates an exemplary embodiment of creating Factor 1 for each patient not included in the full analysis dataset. Factors 2 to 5 are similarly created.

Table 11 is a full set of factors (i.e., Factor 1-Factor 5), which is calculated per patient, and where each of Factors 2-5 can be calculated per patient according to the method used to calculate Table 10 above. These factors are fed into the model equation to obtain a probability value used in predicting early onset glaucoma. That is, the factors in Table 11 are fed into the model equation to collectively transform the five Factors into a probability value used in predicting early onset glaucoma.

TABLE 11

Complete Set of Calculated Factors for the Two Patients

| Variable | Person GS01, OD | Person GS09, OD |
| --- | --- | --- |
| Factor 1 | −0.065479517 | −0.734714313 |
| Factor 2 | −0.172768666 | 1.0103535109 |
| Factor 3 | −0.61092504 | −0.399695528 |
| Factor 4 | −0.85737589 | −2.035040609 |
| Factor 5 | −1.500856668 | −0.963843824 |

Step 3 of the instant exemplary embodiment includes calculating a glaucoma predicted probability per patient (or a glaucoma probability score) using the logistic regression parameter estimates in the formula below:

$$\log it(p_i) = \beta_0 + \beta_1 F_1 + \beta_2 F_2 + \beta_3 F_3 + \beta_4 F_1 F_3 + \beta_5 I(\text{Age}_i \text{ in Category 1}) + \beta_6 I(\text{Age}_i \text{ in Category 2}) + \beta_7 I(\text{Age}_i \text{ in Category 3}) \quad \text{Formula:}$$

Solving the Above Formula for $p_i$ Leads to:

$$p_i = 1 / \left[ 1 + \exp\left\{ \begin{array}{l} -[\beta_0 + \beta_1 F_1 + \beta_2 F_2 + \beta_3 F_3 + \beta_4 F_1 F_3 + \\ \beta_5 I(\text{Age}_i \text{ in Category 1}) + \\ \beta_6 I(\text{Age}_i \text{ in Category 2}) + \\ \beta_7 I(\text{Age}_i \text{ in Category 3})] \end{array} \right\} \right]$$

TABLE 12

Logistic Regression Parameter Estimates

| Parameter | Estimate |
| --- | --- |
| Intercept ($\beta_0$) | −1.6385 |
| Factor 1 ($\beta_1$) | −1.6135 |
| Factor 2 ($\beta_2$) | 5.7379 |
| Factor 3 ($\beta_3$) | −3.5384 |
| Factor 1 * Factor 3 ($\beta_4$) | −1.3297 |
| age_cat (1) ($\beta_5$) | 1.5451 |
| age_cat (2) ($\beta_6$) | −0.2444 |
| age_cat (3) ($\beta_7$) | −1.0383 |

Table 13 is an example of the predicted probability calculations for Each Patient Not Included in the Full Analysis Dataset. Note that Patient GS01 was in Age Category 2 while Patient GS09 was in Age Category 1.

TABLE 13

| Parameter | Person GS01, OD | Person GS09, OD |
| --- | --- | --- |
| Intercept | −1.6385 | −1.6385 |
| Factor 1 | −1.6135 × −0.065479517 = 0.1056512 | −1.6135 × −0.734714313 = 1.185462 |
| Factor 2 | 5.7379 × −0.172768666 = −0.9913293 | 5.7379 × 1.0103535109 = 5.797307 |
| Factor 3 | −3.5384 × −0.61092504 = 2.161697 | −3.5384 × −0.399695528 = 1.414283 |

TABLE 13-continued

| Parameter | Person GS01, OD | Person GS09, OD |
|---|---|---|
| Factor 1 * Factor 3 | −1.3297 × (−0.065479517 × −0.61092504) = −0.05319209 | −1.3297 × (−0.734714313 × −0.399695528) = −0.3904824 |
| age_cat (1) | 1.5451 × 0 = 0 | 1.5451 × 1 = 1.5451 |
| age_cat (2) | −0.2444 × 1 = −0.2444 | −0.2444 × 0 = 0 |
| age_cat (3) | −1.0383 × 0 = 0 | −1.0383 × 0 = 0 |
| Sum (Logit of Predicted Probability): | −0.6600732 | 7.91317 |
| Predicted Probability: | 1/(1 + exp{−(−0.6600732)}) = 0.3407232 | 1/(1 + exp{−(7.91317)}) = 0.9996342 |

As noted above, Table 13 is a predicted probability calculation for each patient not included in the full analysis data set. Patient GS01 was in Age Category 2, while patient GS09 was in Age category 1. The predicted probability (i.e., $p_i$) is any value between approximately 0 and 1. This number is a score and represents a patient's probability in having early onset glaucoma. For example, in the dataset above, patient GS01 has an approximately 34% chance of having early onset glaucoma and patient GS09 has an approximately 99.9% chance of having early onset glaucoma. The probability score between 0 and 1 corresponds to a person having glaucoma from 0% to 100% (i.e., the product of the score and 100 is the percentage). It turns out, that person GS09 did indeed have glaucoma, and GS01 did not.

IV. Model Validation Results:

Table 14 below presents model validation results. In Table 14, examples of patients who were either normal or had glaucoma were tested with the instant model. In most cases (¾), the model confirmed the status of the individuals. In one case (F005), one subject who thought he was normal but classified as having glaucoma by the single variable analysis, was finally declared normal by the model.

TABLE 14

Predictive Model Output for Selected Subjects in the Modeling and Validation Sets (1 indicates glaucoma, 0 indicates no glaucoma)

| | True Status | Predicted Probability | Prediction Status | PIL |
|---|---|---|---|---|
| Modeling Set | | | | |
| EFA GLM | | | | |
| ID #102 | 1 | 1.00 (0.99-1.00) | 1 | 0.014 |
| ID #129 | 1 | 1.00 (0.99-1.00) | 1 | 0.012 |
| ID #F005 | 0 | 0.03 (0.00-0.26) | 0 | 0.259 |
| ID #E062 | 0 | 0.00 (0.00-0.00) | 0 | 0.001 |
| VCDR | | | | |
| ID #102 | 1 | 0.99 (0.95-1.00) | 1 | 0.050 |
| ID #129 | 1 | 0.78 (0.60-0.89) | 1 | 0.295 |
| ID #F005 | 0 | 0.48 (0.32-0.63) | 1 | 0.311 |
| ID #E062 | 0 | 0.00 (0.00-0.00) | 0 | 0.000 |
| Validation Set | | | | |
| EFA GLM | | | | |
| ID #419 | 1 | 1.00 (0.99-1.00) | 1 | 0.005 |
| ID #P1546 | 0 | 0.00 (0.00-0.00) | 0 | 0.006 |
| VCDR | | | | |
| ID #419 | 1 | 0.99 (0.96-1.00) | 1 | 0.041 |
| ID P#1546 | 0 | 0.00 (0.00-0.01) | 0 | 0.010 |

It should be noted that node 100 and its components and functionality described herein constitute a special purpose test node, special purpose computing device, or machine that improves the technological field of eye imaging (e.g., SD-OCT imaging or scanning) by allowing early prediction of glaucoma, thus advantageously reducing a patient's possibility of losing vision. During SD-OCT, reflected light is used to produce detailed cross-sectional and 3D images and measurements of the eye. Node 100 is a special purpose test node and/or computing device configured to input patient-specific SD-OCT parameters and generate an early onset glaucoma prediction score, which cannot be performed manually.

Predicting early onset glaucoma via a prediction node 100 is necessarily rooted in computer technology as it overcomes a problem specifically arising in the realm of computer networks, for example, receiving cross-sectional and 3D measurements or parameters obtained from SD-OCT scans and transforming the parameters into a predictive score via model training and application.

While the subject matter has been has been described herein in reference to specific aspects, embodiments, features, and illustrative embodiments, it will be appreciated that the utility of the subject matter is not thus limited, but rather extends to and encompasses numerous other variations, modifications and alternative embodiments, as will suggest themselves to those of ordinary skill in the field of the present subject matter, based on the disclosure herein.

Some embodiments of the present subject matter can utilize devices, systems, methods, and/or computer readable media as, such as described in any of the following publications, each publication of which is hereby incorporated by reference as if set forth fully herein:

[1] Kingman S. Glaucoma is second leading cause of blindness globally. Bull World Health Organ. 2004; 82:887-888.

[2] Quigley H A, Broman A T. The number of people with glaucoma worldwide in 2010 and 2020. Br J Ophthalmol. 2006; 90:262-267.

[3] Friedman D S, Wolfs R C, O'Colmain B J, et al. Prevalence of open-angle glaucoma among adults in the United States. Arch Ophthalmol. 2004; 122:532-538.

[4] Mikelberg F S, Yidegiligne H M, Schulzer M. Optic nerve axon count and axon diameter in patients with ocular hypertension and normal visual fields. Ophthalmology. 1995; 102:342-348.

[5] Quigley H A, Addicks E M, Green W R. Optic nerve damage in human glaucoma. Ill. Quantitative correlation of nerve fiber loss and visual field defect in glaucoma, ischemic neuropathy, papilledema, and toxic neuropathy. Arch Ophthalmol. 1982; 100:135-146.

[6] Tielsch J M, Katz J, Quigley H A, Miller N R, Sommer A. Intraobserver and interobserver agreement in measurement of optic disc characteristics. Ophthalmology. 1988; 95:350-356.

[7] Azuara-Blanco A, Katz L J, Spaeth G L, Vernon S A, Spencer F, Lanzl I M. Clinical agreement among glaucoma experts in the detection of glaucomatous changes of the optic disk using simultaneous stereoscopic photographs. Am J Ophthalmol. 2003; 136:949-950.

[8] Badala F, Nouri-Mandavi K, Raoof D A, Leeprechanon N, Law S K, Caprioli J. Optic disc and nerve fiber layer imaging to detect glaucoma. Arch Ophthalmol. 2007; 144:724-732.

[9] Medeiros F A, Zangwill L M, Bowd C, Vessani R M, Susanna R Jr, Weinreb R N. Evaluation of retinal nerve fiber layer, optic nerve head, and macular thickness measurements for glaucoma detection using optical coherence tomography. Am J Ophthalmol. 2005; 139:44-55.

[10] Ford B A, Artes P H, McCormick T A, Nicolela M T, LeBlanc R P, Chauhan B C. Comparison of data analysis tools for detection of glaucoma with the Heidelberg Retina Tomograph. Ophthalmology. 2003; 110:1145-1150.

[11] Magacho L, Marcondes A M, Costa V P. Discrimination between normal and glaucomatous eyes with scanning laser polarimetry and optic disc topography: a preliminary report. Eur J Ophthalmol. 2005; 15:353-359.

[12] Toth M, Kothy P, Hollo G. Accuracy of scanning laser polarimetry, scanning laser tomography, and their combination in a glaucoma screening trial. J Glaucoma. 2008; 17:639-646.

[13] Baskaran M, Ong E L, Li J L, et al. Classification algorithms enhance the discrimination of glaucoma from normal eyes using high-definition optical coherence tomography. Invest Ophthalmol Vis Sci. 2012; 53:2314-2320.

[14] Fang Y, Pan Y Z, Li M, Qiao R H, Cai Y. Diagnostic capability of Fourier-Domain optical coherence tomography in early primary open angle glaucoma. Chin Med J (Engl). 2010; 123: 2045-2050.

[15] Huang J Y, Pekmezci M, Mesiwala N, Kao A, Lin S. Diagnostic power of optic disc morphology, peripapillary retinal nerve fiber layer thickness, and macular inner retinal layer thickness in glaucoma diagnosis with fourier-domain optical coherence tomography. J Glaucoma. 2011; 20:87-94.

[16] Mwanza J C, Oakley J D, Budenz D L, Chang R T, Knight O J, Feuer W J. Macular ganglion cell-inner plexiform layer: automated detection and thickness reproducibility with spectral domain-optical coherence tomography in glaucoma. Invest Ophthalmol Vis Sci. 2011; 52:8323-8329.

[17] Mwanza J C, Oakley J D, Budenz D L, Anderson D R. Ability of cirrus HD-OCT optic nerve head parameters to discriminate normal from glaucomatous eyes. Ophthalmology. 2011; 118: 241-248.

[18] Mwanza J C, Durbin M K, Budenz D L, et al. Glaucoma diagnostic accuracy of ganglion cell-inner plexiform layer thickness: comparison with nerve fiber layer and optic nerve head. Ophthalmology. 2012; 119:1151-1158.

[19] Jöreskog K G. How large can a standardized coefficient be? SSI. 1999:1-3. Available at http://www.ssicentral.com/lisrel/techdocs/HowLargeCanaStandardizedCoefficientbe.pdf. Accessed Sep. 13, 2013.

[20] Hair J F, Black W C, Babin B J, Anderson R E. Multivariate Data Analysis. 7th ed. Upper Saddle River, N J: Prentice Hall; 2009.

[21] Burhman K P, Anderdon D R. Multimodel inference: understanding AIC and BIC in model selection. Sociol Methods Res. 2004; 33:261-304.

[22] DeLong E R, DeLong D M, Clarke-Pearson D L. Comparing the areas under two or more correlated receiver operating characteristic curves: a nonparametric approach. Biometrics. 1988; 44:837-845.

[23] Budenz D L, Michael A, Chang R T, McSoley J, Katz J. Sensitivity and specificity of the StratusOCT for perimetric glaucoma. Ophthalmology. 2005; 112:3-9.

[24] lester M, Mardin C Y, Budde W M, Junemann A G, Hayler J K, Jonas J B. Discriminate analysis formulas of optic nerve head parameters measured by confocal scanning laser tomography. J Glaucoma. 2002; 11:97-104.

[25] Lu A T, Wang M, Varma R, et al. Combining nerve fiber layer parameters to optimize glaucoma diagnosis with optical coherence tomography. Ophthalmology. 2008; 115:1352-1357.

[26] Wang M, Lu A T, Varma R, Schuman J S, Greenfield D S, Huang D. Combining information from 3 anatomic regions in the diagnosis of glaucoma with time-domain optical coherence tomography [published online ahead print Jun. 23, 2012]. J Glaucoma. doi:10.1097/IJG.0b013e318264b941

[27] Bathija R, Zangwill L, Berry C C, Sample P A, Weinreb R N. Detection of early glaucomatous structural damage with confocal scanning laser tomography. J Glaucoma. 1998; 7:121-127.

[28] Mikelberg F S, Parfitt C M, Swindale N V, Graham S L, Drance S M, Gosine R. Ability of the Heidelberg retina tomograph to detect early glaucomatous visual field loss. J Glaucoma. 1995; 4:242-247.

[29] Burk R O, Noack H, Rohrschneider K, Volcker H E. Prediction of glaucomatous visual field defects by reference plane independent three-dimensional optic nerve head parameters. In: Wall M, Wild J M, eds. XIIIth International Perimetric Society Meeting. Gardone Riviera, Italy: Kugler; 1998:463-474.

[30] Ferreras A, Pablo E, Larrosa J M, Polo V, Pajarin A B, Honrubia F M. Discriminating between normal and glaucoma-damaged eyes with the Heidelberg Retina Tomograph 3. Ophthalmology. 2008; 115:775-781.

[31] lester M, Jonas J B, Mardin C Y, Budde W M. Discriminant analysis models for early glaucoma detection of glaucomatous optic disc changes. Br J Ophthalmol. 2000; 84:464-468.

[32] Mardin C Y, Horn F K, Jonas J B, Budde W M. Preperimetric glaucoma diagnosis by confocal scanning laser tomography of the optic disc. Br J Ophthalmol. 1999; 83:299-304.

[33] lester M, Swindale N V, Mikelberg F S. Sector-based analysis of optic nerve head shape parameters and visual field indices in healthy and glaucomatous eyes. J Glaucoma. 1997; 6:370-376.

[34] Fabrigar L R, Wegener D T, MacCallum R C, Strahan E J. Evaluating the use of explanatory factor analysis in psychological research. Psychol Methods. 1999; 4:272-299.

[35] Huang M L, Chen H Y. Development and comparison of automated classifiers for glaucoma diagnosis using Stratus optical coherence tomography. Invest Ophthalmol Vis Sci. 2005; 46:4121-4129.

[36] Gorsuch R L. Common factor-analysis versus component analysis—some well and little known facts. Mutivariate Behav Res. 1990; 25:33-39.

[37] McArdle J J. Principles versus principals of structural factor analyses. Multivariate Behav Res. 1990; 25:81-87.

[38] Gorsuch R L. Exploratory factor analysis: its role in item analysis. J Pers Assess. 1997; 68:532-560.

The disclosures of the foregoing publications (i.e., [1] to [38]) above are hereby incorporated by reference as if set forth fully herein.

Various combinations and sub-combinations of the structures, machines, functionality, and/or features described herein are contemplated and will be apparent to a skilled person having knowledge of this disclosure. Any of the various features and elements as disclosed herein can be combined with one or more other disclosed features and elements unless indicated to the contrary herein. Correspondingly, the subject matter as hereinafter claimed is intended to be broadly construed and interpreted, as including all such variations, modifications and alternative embodiments, within its scope and including equivalents of the claims.

What is claimed is:

1. A method of predicting early onset glaucoma, the method comprising:
obtaining a set of patient-specific structural parameters via Spectral Domain Optical Coherence Tomography (SD-OCT), the set of patient-specific structural parameters including Optic Nerve Head (ONH) parameters, peripapillary Retinal Nerve Fiber Layer (RNFL) parameters, and Ganglion Cell-Inner Plexiform Layer (GCIPL) parameters;
generating a glaucoma probability score based upon the set of patient-specific parameters and a model dataset associated with plurality of patients; and
treating a patient based upon the glaucoma probability score.

2. The method of claim 1, wherein the ONH parameters include a rim area, a Cup-to-Disc Ratio (CDR), or a Vertical Cup-to-Disc diameter Ratio (VCDR).

3. The method of claim 1, wherein the peripapillary RNFL parameters include average and quadrant thicknesses.

4. The method of claim 3, wherein the quadrant thicknesses include a superior quadrant thickness, a nasal quadrant thickness, an inferior quadrant thickness, and a temporal quadrant thickness.

5. The method of claim 1, wherein the GCIPL parameters include an average GCIPL thickness, a minimum GCIPL thickness, and one or more sectoral thicknesses as measured along a given radial spoke in the elliptical annulus.

6. The method of claim 5, wherein the sectoral thicknesses include a superior thickness, a superonasal thickness, an inferonasal thickness, an inferior thickness, an inferotemporal thickness, and a superotemporal thickness.

7. The method of claim 1, wherein the glaucoma probability score is modeled using a multivariable logistic regression model fitted to the model dataset.

8. The method of claim 7, wherein the multivariable logistic regression model includes a set of estimated factors scores estimated via Exploratory Factor Analysis (EFA) for each factor and patient-specific structural parameter combination.

9. The method of claim 1, wherein the glaucoma probability score is a whole number integer between 0 and 1.

10. The method of claim 1, wherein the model dataset is in a storage element accessed by a glaucoma predicting module.

11. A system of predicting early onset glaucoma, the system comprising:
a glaucoma predicting module (GPM) residing at a computing platform node, the GPM being configured to obtain a set of patient-specific structural parameters, the set of parameters including Optic Nerve Head (ONH) parameters, peripapillary Retinal Nerve Fiber Layer (RNFL) parameters, and Ganglion Cell-Inner Plexiform Layer (GCIPL) parameters measured via Spectral Domain Optical Coherence Tomography (SD-OCT); and
wherein the GMP is configured to generate a glaucoma probability score using the set of patient-specific parameters and a model dataset stored in a database.

12. The system of claim 11, wherein the ONH parameters include a rim area, a Cup-to-Disc Ratio (CDR), or a Vertical Cup-to-Disc diameter Ratio (VCDR).

13. The system of claim 11, wherein the peripapillary RNFL parameters include average and quadrant thicknesses.

14. The system of claim 13, wherein the quadrant thicknesses include a superior quadrant thickness, a nasal quadrant thickness, an inferior quadrant thickness, and a temporal quadrant thickness.

15. The system of claim 11, wherein the GCIPL parameters include an average GCIPL thickness, a minimum GCIPL thickness, and one or more sectoral thicknesses as measured along a given radial spoke in the elliptical annulus.

16. The system of claim 15, wherein the sectoral thicknesses include a superior thickness, a superonasal thickness, an inferonasal thickness, an inferior thickness, an inferotemporal thickness, and a superotemporal thickness.

17. The system of claim 11, wherein the glaucoma probability score is modeled using a multivariable logistic regression model fitted to the model dataset.

18. The system of claim 11, wherein the multivariable logistic regression model includes a set of estimated factors scores estimated via Exploratory Factor Analysis (EFA) for each factor and patient-specific structural parameter combination.

19. A non-transitory computer readable medium having stored thereon executable instructions that when executed by a processor of a computer control the computer to perform steps comprising:
obtaining a set of patient-specific structural parameters via Spectral Domain Optical Coherence Tomography (SD-OCT), the set of patient-specific structural parameters including Optic Nerve Head (ONH) parameters, peripapillary Retinal Nerve Fiber Layer (RNFL) parameters, and Ganglion Cell-Inner Plexiform Layer (GCIPL) parameters;
generating a glaucoma probability score based upon the set of patient-specific parameters and a model dataset associated with plurality of patients.

* * * * *